US011684658B2

(12) United States Patent
Tuohy et al.

(10) Patent No.: US 11,684,658 B2
(45) Date of Patent: Jun. 27, 2023

(54) VACCINE ADJUVANTS AND FORMULATIONS

(71) Applicant: The Cleveland Clinic Foundation, Cleveland, OH (US)

(72) Inventors: Vincent K. Tuohy, Broadview Heights, OH (US); Justin M. Johnson, Willoughby Hills, OH (US)

(73) Assignee: CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 16/641,819

(22) PCT Filed: Feb. 13, 2020

(86) PCT No.: PCT/US2020/018186
§ 371 (c)(1),
(2) Date: Feb. 25, 2020

(87) PCT Pub. No.: WO2020/168126
PCT Pub. Date: Aug. 20, 2020

(65) Prior Publication Data
US 2021/0386839 A1    Dec. 16, 2021

Related U.S. Application Data

(60) Provisional application No. 62/806,422, filed on Feb. 15, 2019.

(51) Int. Cl.
| | | |
|---|---|---|
| *A61K 39/00* | (2006.01) | |
| *A61P 35/00* | (2006.01) | |
| *A61K 33/243* | (2019.01) | |
| *A61K 9/107* | (2006.01) | |
| *A61K 31/282* | (2006.01) | |
| *A61K 31/337* | (2006.01) | |
| *A61K 31/4196* | (2006.01) | |
| *A61K 31/502* | (2006.01) | |
| *A61K 31/675* | (2006.01) | |
| *A61K 31/704* | (2006.01) | |
| *A61K 31/7048* | (2006.01) | |
| *A61K 31/7068* | (2006.01) | |
| *A61K 38/14* | (2006.01) | |
| *A61K 39/39* | (2006.01) | |
| *A61K 45/06* | (2006.01) | |
| *A61K 47/44* | (2017.01) | |

(52) U.S. Cl.
CPC .......... *A61K 39/0011* (2013.01); *A61K 9/107* (2013.01); *A61K 31/282* (2013.01); *A61K 31/337* (2013.01); *A61K 31/4196* (2013.01); *A61K 31/502* (2013.01); *A61K 31/675* (2013.01); *A61K 31/704* (2013.01); *A61K 31/7048* (2013.01); *A61K 31/7068* (2013.01); *A61K 33/243* (2019.01); *A61K 38/14* (2013.01); *A61K 39/39* (2013.01); *A61K 45/06* (2013.01); *A61K 47/44* (2013.01); *A61P 35/00* (2018.01); *A61K 2039/545* (2013.01); *A61K 2039/55583* (2013.01)

(58) Field of Classification Search
CPC ........................... A61K 39/0011; A61P 35/00
See application file for complete search history.

(56) References Cited

U.S. PATENT DOCUMENTS

2013/0129756 A1    5/2013  Gorvel et al.
2013/0287836 A1   10/2013  Ingber et al.

FOREIGN PATENT DOCUMENTS

WO    WO 2017/079303    5/2017

OTHER PUBLICATIONS

International Search Report and Written Opinion for PCT/US20/18186, dated Jun. 3, 2020. 10 pages.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
CTCAE version 5. 2017. 147 pages.
De Gregorio et al., Vaccine adjuvants: mode of action. Front Immunol. Jul. 31, 2013;4:214.
ECOG (Eastern Performancy Oncology Group) Performance Status 0-1. Retrieved from the internet 2022. 1 page.
Guy et al., Induction of mammary tumors by expression of polyomavirus middle T oncogene: a transgenic mouse model for metastatic disease. Mol Cell Biol. Mar. 1992;12(3):954-61.
Guy et al., Expression of the neu protooncogene in the mammary epithelium of transgenic mice induces metastatic disease. Proc Natl Acad Sci U S A. Nov. 15, 1992;89(22):10578-82.
Huang et al., Characterization and optimization of the glucan particle-based vaccine platform. Clin Vaccine Immunol. Oct. 2013;20(10):1585-91.
Karlin et al., Applications and statistics for multiple high-scoring segments in molecular sequences. Proc Natl Acad Sci U S A. Jun. 15, 1993;90(12):5873-7.
Karlin et al., Methods for assessing the statistical significance of molecular sequence features by using general scoring schemes. Proc Natl Acad Sci U S A. Mar. 1990;87(6):2264-8.

(Continued)

*Primary Examiner* — Kevin E Weddington
(74) *Attorney, Agent, or Firm* — Casimir Jones, S.C; Jason R. Bond

(57) ABSTRACT

Compositions comprising an antigen, a carbohydrate, and a metabolizable oil, methods of administering such compositions to a subject, methods of making such compounds, and related compositions, methods, and uses.

10 Claims, 17 Drawing Sheets

Specification includes a Sequence Listing.

(56) References Cited

OTHER PUBLICATIONS

Leenaars et al., Assessment of side effects induced by injection of different adjuvant/antigen combinations in rabbits and mice. Lab Anim. Oct. 1998;32(4):387-406.

Leenaars et al., Immune responses and side effects of five different oil-based adjuvants in mice. Vet Immunol Immunopathol. Feb. 27, 1998;61(2-4):291-304.

Luger et al., Either a Th17 or a Th1 effector response can drive autoimmunity: conditions of disease induction affect dominant effector category. J Exp Med. Apr. 14, 2008;205(4):799-810.

Oken et al., Toxicity and response criteria of the Eastern Cooperative Oncology Group. Am J Clin Oncol. Dec. 1982;5(6):649-55.

Steinman. A brief history of T(H)17, the first major revision in the T(H)1/T(H)2 hypothesis of T cell-mediated tissue damage. Nat Med. Feb. 2007;13(2):139-45.

*Group A Mice – Normalized Body Weight Changes from Time of First Vaccination.*

(Arrow indicates day of first vaccination)

*Group B Mice – Normalized Body Weight Changes from Time of First Vaccination.*

(Arrows indicate days of each of 2 vaccinations)

*Group C Mice – Normalized Body Weight Changes from Time of First Vaccination.*

(Arrows indicate days of each of 3 vaccinations)

*Group A Mice – Normalized Body Temperature Changes from Time of First Vaccination.*

(Arrow indicates day of first vaccination)

*Group B Mice – Normalized Body Temperature Changes from Time of First Vaccination.*

(Arrows indicate days of each of 2 vaccinations)

*Group C Mice – Normalized Body Temperature Changes from Time of First Vaccination.*

(Arrows indicate days of each of 3 vaccinations)

SEQUENCE LISTING

<160> NUMBER OF SEQ ID NOS: 5

<210> SEQ ID NO 1
<211> LENGTH: 142
<212> TYPE: PRT
<213> ORGANISM: Homo sapiens

<400> SEQUENCE: 1

Met Arg Phe Phe Val Pro Leu Phe Leu Val Gly Ile Leu Phe Pro Ala
1               5                   10                  15

Ile Leu Ala Lys Gln Phe Thr Lys Cys Glu Leu Ser Gln Leu Leu Lys
            20                  25                  30

Asp Ile Asp Gly Tyr Gly Gly Ile Ala Leu Pro Glu Leu Ile Cys Thr
        35                  40                  45

Met Phe His Thr Ser Gly Tyr Asp Thr Gln Ala Ile Val Glu Asn Asn
    50                  55                  60

Glu Ser Thr Glu Tyr Gly Leu Phe Gln Ile Ser Asn Lys Leu Trp Cys
65                  70                  75                  80

Lys Ser Ser Gln Val Pro Gln Ser Arg Asn Ile Cys Asp Ile Ser Cys
                85                  90                  95

Asp Lys Phe Leu Asp Asp Asp Ile Thr Asp Asp Ile Met Cys Ala Lys
            100                 105                 110

Lys Ile Leu Asp Ile Lys Gly Ile Asp Tyr Trp Leu Ala His Lys Ala
        115                 120                 125

Leu Cys Thr Glu Lys Leu Glu Gln Trp Leu Cys Glu Lys Leu
    130                 135                 140

<210> SEQ ID NO 2
<211> LENGTH: 742
<212> TYPE: DNA
<213> ORGANISM: Homo sapiens

<400> SEQUENCE: 2
atttcaggtt cttgggggta gccaaaatga ggttctttgt ccctctgttc ctggtgggca      60
tcctgttccc tgccatcctg gccaagcaat tcacaaaatg tgagctgtcc cagctgctga     120
aagacataga tggttatgga ggcatcgctt tgcctgaatt gatctgtacc atgtttcaca     180
ccagtggtta tgacacacaa gccatagttg aaaacaatga agcacggaa tatggactct      240 tccagatcag taataagctt tggtgcaaga gcagccaggt ccctcagtca aggaacatct     300
gtgacatctc ctgtgacaag ttcctggatg atgacattac tgatgacata atgtgtgcca     360
agaagatcct ggatattaaa ggaattgact actggttggc ccataaagcc ctctgcactg     420
agaagctgga acagtggctt tgtgagaagt tgtgagtgtc tgctgtcctt ggcacccctg     480
cccactccac actcctggaa tacctcttcc ctaatgccac ctcagtttgt ttctttctgt     540
tcccccaaag cttatctgtc tctgagcctt gggccctgta gtgacatcac cgaattcttg     600
aagactattt tccagggatg cctgagtggt gcactgagct ctagacccctt actcagtgcc    660 ttcgatggca ctttcactac agcacagatt tcacctctgt cttgaataaa ggtcccactt     720
tgaagtcaaa aaaaaaaaaa aa                                               742

<210> SEQ ID NO 3
<211> LENGTH: 143
<212> TYPE: PRT
<213> ORGANISM: Mus musculus

<400> SEQUENCE: 3

```
Met Met His Phe Val Pro Leu Phe Leu Val Cys Ile Leu Ser Leu Pro
1               5                   10                  15

Ala Phe Gln Ala Thr Glu Leu Thr Lys Cys Lys Val Ser His Ala Ile
            20                  25                  30

Lys Asp Ile Asp Gly Tyr Gln Gly Ile Ser Leu Leu Glu Trp Ala Cys
            35                  40                  45

Val Leu Phe His Thr Ser Gly Tyr Asp Thr Gln Ala Val Val Asn Asp
    50                  55                  60

Asn Gly Ser Thr Glu Tyr Gly Leu Phe Gln Ile Ser Asp Arg Phe Trp
65                  70                  75                  80

Cys Lys Ser Ser Glu Phe Pro Glu Ser Glu Asn Ile Cys Gly Ile Ser
                85                  90                  95

Cys Asp Lys Leu Leu Asp Asp Glu Leu Asp Asp Ile Ala Cys Ala
                100                 105                 110

Lys Lys Ile Leu Ala Ile Lys Gly Ile Asp Tyr Trp Lys Ala Tyr Lys
            115                 120                 125

Pro Met Cys Ser Glu Lys Leu Glu Gln Trp Arg Cys Glu Lys Pro
    130                 135                 140
```

<210> SEQ ID NO 4
<211> LENGTH: 733
<212> TYPE: DNA
<213> ORGANISM: Mus musculus

<400> SEQUENCE: 4

```
ggagcagtca aaatgatgca tttcgttcct tgttcctgg tgtgtatttt gtcgttgcct      60
gcctttcaag ccacagagct tacaaaatgc aaggtgtccc atgccattaa agacatagat    120
ggctatcaag gcatctcttt gcttgaatgg gcctgtgttt tatttcatac cagtggctac    180
gacacacaag ctgttgtcaa cgacaacggc agcacagagt acggactctt ccagatcagt    240
gacagatttt ggtgtaaaag tagtgagttc cccgagtcgg agaacatctg tggcatctcc    300
tgtgacaagt tattggatga cgagttggat gatgacatag cgtgtgccaa gaagatcctg    360
gctatcaaag gaatcgacta ctggaaagcc tacaagccca tgtgctctga agcttgaa     420
cagtggcgtt gtgagaagcc ctgagccccc ccccccccc ccccgtcct tgctgctcct     480
gccccgtggt caggaatgcc tcttccctaa ggctacctca gcttggctct tgctattcct    540
gtgaagatga tctgcctctg agccttgtac cctgtagtga caccaccgga ctctagagga    600
ctttttttc cctatgggag tgtgactggc gcactggact gcaaacccttgcttagtgac       660
ggcgagggtc tcgatggggg ttttacaaaa tcgagagagc cctctcctgt cccaaataaa    720
gggccagact tga                                                       733
```

<210> SEQ ID NO 5
<211> LENGTH: 123
<212> TYPE: PRT
<213> ORGANISM: Homo sapiens

<400> SEQUENCE: 5

```
Lys Gln Phe Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Phe His
            20                  25                  30

Thr Ser Gly Tyr Asp Thr Gln Ala Ile Val Glu Asn Asn Glu Ser Thr
            35                  40                  45

Glu Tyr Gly Leu Phe Gln Ile Ser Asn Lys Leu Trp Cys Lys Ser Ser
```

```
                50                      55                      60
Gln Val Pro Gln Ser Arg Asn Ile Cys Asp Ile Ser Cys Asp Lys Phe
 65                      70                      75                      80

Leu Asp Asp Asp Ile Thr Asp Asp Ile Met Cys Ala Lys Lys Ile Leu
                        85                      90                      95

Asp Ile Lys Gly Ile Asp Tyr Trp Leu Ala His Lys Ala Leu Cys Thr
                100                     105                     110

Glu Lys Leu Glu Gln Trp Leu Cys Glu Lys Leu
            115                     120
```

VACCINE ADJUVANTS AND FORMULATIONS

RELATED APPLICATION

The present application claims priority to U.S. Provisional Patent Application No. 62/806,422 filed Feb. 15, 2019, the entire contents of which are hereby incorporated by reference for all purposes.

SEQUENCE LISTING

The present specification makes reference to a Sequence Listing (submitted electronically as a .txt file named "CCI_005_Seq_Listing.txt" on Feb. 13, 2020). The .txt file was generated on Feb. 13, 2020 and is 6 kb in size. The entire contents of the Sequence Listing are herein incorporated by reference.

BACKGROUND

Vaccines generally contain at least two major components: an immunogen that serves as a target for an adaptive immune response, and an adjuvant that enhances the adaptive immune response. Complete Freund's Adjuvant (CFA) is a suspension of dead mycobacteria in a liquid prepared from non-metabolizable oils. CFA is widely considered the "gold standard" to which all other adjuvants are compared because of its proven effectiveness for over 70 years in inducing adaptive immunity. However, CFA cannot be used as an adjuvant in human vaccination because of its toxic effects primarily related to its induction of unresolved granulomas and abscesses at the site of vaccination.

Thus, there is a need for an adjuvant that is suitable for human vaccination that can also facilitate the induction of a robust immune response.

Breast cancer is the second most frequent cause of cancer-related deaths among women. There are several different genetic subtypes of breast cancer, and treatments are commonly directed to particular subtypes. For example, hormone therapies and drugs that target estrogen receptors (ERs) are designed to treat ER-positive cancers. Triple-negative breast cancer (TNBC) is the most aggressive and most lethal form of breast cancer and is notoriously difficult to treat. TNBC cancer cells are negative for estrogen receptor (ER), progesterone (PR), and HER2, so drugs designed to treat those receptors are ineffective for TNBC.

There is a need for breast cancer treatments that are effective against difficult-to-treat subtypes of breast cancer, including TNBC.

SUMMARY

Most current clinical vaccine formulations induce a response from pro-inflammatory type-1 T cells that produce interferon-gamma (IFNγ) but little, if any, response from type-17 T cells that produce interleukin-17 (IL-17). The present invention encompasses the insight that many current clinical vaccine formulations are not effective because they do not elicit both type-1 and type-17 immune responses. In accordance with the present invention, provided are compositions that induce immune responses comprising both type-1 and type-17 T cells while inducing limited or no toxicity.

The present invention also encompasses the development of vaccine formulations that induce an adaptive immune response effective to inhibit and/or prevent breast cancer growth. Presently disclosed compositions comprise an α-lactalbumin polypeptide antigen and adjuvant components as described further herein. α-lactalbumin is constitutively overexpressed in the majority of TNBC and in a lower percentage of other forms of breast tumors. Therefore, the presently disclosed vaccine formulations, compositions, and methods, may be useful in treating and/or preventing the most aggressive breast cancers.

In one aspect, provided are compositions comprising: a carbohydrate, and a metabolizable oil, wherein (i) the composition further comprises an antigen, or (ii) the carbohydrate comprises a polysaccharide and the composition comprises a mixture of at least two polysaccharides.

In some embodiments, the antigen is a tumor-associated antigen.

In some embodiments, the carbohydrate comprises a polysaccharide and the composition comprises a mixture of at least two polysaccharides.

In some embodiments, the composition comprises a tumor-associated antigen, the carbohydrate comprises a polysaccharide, and the composition comprises a mixture of at least two polysaccharides.

In some embodiments, the composition of (i) comprising an antigen or of (ii) further comprising an antigen are capable of inducing an antigen-specific T cell immune response comprising both a type-1 and a type-17 proinflammatory T cell response when administered to a subject.

In some embodiments, the carbohydrate binds to a pattern recognition receptor. For example, the pattern recognition receptor may be TLR2 or dectin-1.

In some embodiments, the mixture of polysaccharides comprises at least three polysaccharides.

In some embodiments, the polysaccharide or each polysaccharide in the mixture is selected from the group consisting of chitin, dextran, glucan, lentanan, mannan, and combinations thereof.

In some embodiments, the polysaccharide or mixture of polysaccharides comprises a glucan, for example, a β-glucan (e.g., a 1-3 β-glucan). For example, the mixture of polysaccharides may comprise a mixture of chitins, glucans, and mannans. In some embodiments, at least 50% of the carbohydrates in the composition are β-glucans.

In some embodiments, the composition comprises zymosan.

In some embodiments, the metabolizable oil comprises a purified oil. For example, the purified oil may be mineral oil, e.g., DRAKEOL™ 6 VR.

In some embodiments, the metabolizable oil comprises a biodegradable oil. For example, the biodegradable oil may be isopropyl myristate, squalene oil, squalane oil, a vegetable oil, or a combination thereof. In some embodiments, the biodegradable oil is a vegetable oil, such as, for example, a vegetable oil selected from the group consisting of almond oil, castor oil, chaulmoogra oil, coconut oil, corn oil, cottonseed oil, olive oil, peanut oil, persic oil, safflower oil, and soya bean oil.

In some embodiments, the metabolizable oil is a pharmaceutical grade oil.

In some embodiments, the composition further comprises a surfactant, for example, mannide monooleate, isomannide monooleate, or a combination thereof. In some embodiments, the surfactant comprises mannide monooleate. For example, the composition may comprise MONTANIDE™, such as MONTANIDE™ ISA 51 VG.

In some embodiments, the composition is an emulsion of water and oil, for example, a water-in-oil emulsion.

In some embodiments, the antigen comprises a polypeptide antigen. In some embodiments, the polypeptide antigen is a retired self-antigen.

In some embodiments, the polypeptide antigen comprises an α-lactalbumin polypeptide. For example, the α-lactalbumin polypeptide may have an amino acid sequence that comprises at least 8 consecutive amino acids of SEQ ID NO: 5.

In some embodiments, the antigen and the carbohydrate (or mixture of polysaccharides) are present in a ratio of from about 10:1 to about 1:10 (w/w). In some embodiments, the antigen and the carbohydrate (or mixture of polysaccharides) are present in a ratio of about 1:1 (w/w).

In some embodiments, the composition further comprises a pharmaceutically acceptable carrier.

In some embodiments, the composition further comprises an antibiotic.

In one aspect, provided are methods comprising a step of administering to a subject a therapeutically effective amount of a composition as disclosed herein, e.g., a composition comprising an antigen, a carbohydrate, and a metabolizable oil.

In some embodiments, the subject is a mammal, for example, a human.

In some embodiments, the subject is a non-lactating female subject.

In some embodiments, the subject has cancer or is at risk of developing cancer.

In some embodiments, the subject has not been diagnosed with cancer.

In some embodiments, the cancer is breast cancer, for example, a metastatic breast cancer, a primary breast cancer, and/or a triple-negative breast cancer.

In some embodiments, the cancer comprises cells that overexpress α-lactalbumin.

In some embodiments, the therapeutically effective amount comprises more than one dose, for example, three or more doses. In some embodiments, the therapeutically effective amount comprises no more than three doses.

In some embodiments, each dose is administered one or more weeks apart, for example, at least four weeks apart. In some embodiments, each dose is administered about four weeks apart.

In some embodiments, each dose contains approximately the same amount of antigen. In some embodiments, each dose contains approximately the same amount of antigen and the same amount of carbohydrate.

In some embodiments, each dose contains between about 1 μg to about 5 mg of antigen, for example, between about 50 μg to about 2 mg of antigen, or between about 100 μg to about 1 mg of antigen.

In some embodiments, the composition is administered by subcutaneous, intradermal, subdermal, or intramuscular injection.

In some embodiments, administering the composition induces an antigen-specific T cell immune response. In some embodiments, the T cell immune response comprises CD4+ T cells, CD8+ T cells, or both. In some embodiments, the T cell immune response comprises a type-1 or a type-17 proinflammatory T cell response. In some embodiments, the T cell immune response comprises both a type-1 and a type-17 proinflammatory T cell response.

In some embodiments, administering causes reduced granuloma formation relative to a reference level, for example, the level of granuloma formation observed in a subject administered a composition comprising Complete Freund's Adjuvant.

In some embodiments, the subject has been administered, will be administered, or is simultaneously administered an additional anti-cancer therapy, for example, an anti-cancer therapy that comprises an anti-cancer agent. In some embodiments, the additional anti-cancer agent is selected from the group consisting of bevacizumab, bleomycin, carboplatin, cisplatin, cyclophosphamide, docetaxel, doxorubicin, etoposide, gemcitabine, letrozole, olaparib, tamoxifen, topotecan, trabectedin, a CTLA4 antibody, a PD-1 antibody, a PD-L1 antibody, and a TGFβ antibody.

In some embodiments, provided are compositions comprising an α-lactalbumin polypeptide, zymosan, and MONTANIDE™, wherein the α-lactalbumin polypeptide comprises an amino acid sequence that is at least 80%, 85%, 90%, or 95% identical to the amino acid sequence of SEQ ID NO: 5. In some embodiments, the α-lactalbumin polypeptide comprises an amino acid sequence that is 100% identical to the amino acid sequence of SEQ ID NO: 5.

In one aspect, provided are formulations comprising a water-in-oil emulsion of α-lactalbumin polypeptide, zymosan, and MONTANIDE™, wherein the α-lactalbumin polypeptide and zymosan are present in the formulation at a ratio of between about 1:5 (w/w) and 5:1 (w/w), and wherein the α-lactalbumin polypeptide comprises an amino acid sequence that is at least 80%, 85%, 90%, or 95% identical to the amino acid sequence of SEQ ID NO: 5. In some embodiments, the α-lactalbumin polypeptide comprises an amino acid sequence that is 100% identical to the amino acid sequence of SEQ ID NO: 5.

In one aspect, provided are methods of making a composition or formulation disclosed herein, comprising a step of mixing an aqueous solution comprising the antigen with an emulsion comprising the carbohydrate and the metabolizable oil. In some embodiments, the ratio of the aqueous solution to the emulsion is between about 1:2 to about 2:1 (v/v), for example, about 1:1 (v/v).

In one aspect, provided are uses of a composition or formulation as disclosed herein for the manufacture of a medicament for preventing, treating, or ameliorating cancer.

BRIEF DESCRIPTION OF THE DRAWINGS

FIG. 3A shows that female BALB/cJ mice were vaccinated subcutaneously at 6-8 weeks of age with 200 μL of an emulsion containing 100 μg recombinant mouse α-lactalbumin and 200 μg CFA. Control mice were vaccinated with 200 μg CFA alone. Two weeks after vaccination, mice were inoculated subcutaneously with $2\times10^4$ 4 T1 mouse breast tumor cells, and tumor growth was measured every other day using a vernier caliper. This same protocol was subsequently used to determine tumor growth using doses recommended by each manufacturer for the various other adjuvants indicated in FIG. 2 including (FIG. 3B) GPI-0100×2, (FIG. 3C) Sigma Lipid A, (FIG. 3D) AS02B Lipid A, (FIG. 3E) CpG DNA×2, (FIG. 3F) CpG DNA+α-Gal-Cer×2, (FIG. 3G) β-Glucan Peptide in IFA, and (FIG. 3H) zymosan in IFA. Some vaccinations were performed twice, two weeks apart and are indicated as ×2. Asterisks indicate significant differences (P<0.05) between test and control vaccinated mice.

FIG. 15 is a photograph of mice taken approximately two weeks after a second injection and approximately 6 weeks after a first injection. Blue arrows indicate first injection sites, and red arrows indicate second injection sites. As FIG. 15 shows, first injection sites exhibited improved appearances relative to second injection sites, indicating resolution of granulomas over time.

DETAILED DESCRIPTION

Figure 1:
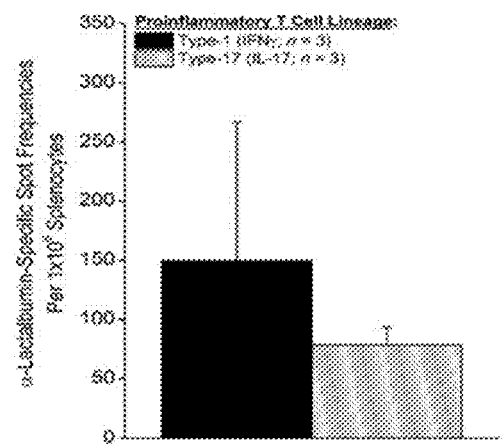
FIG. 1 shows induction of proinflammatory T cell immunity by vaccination with α-lactalbumin/Complete Freund's adjuvant (CFA) Emulsions. Mean splenocyte frequencies of IFNγ (type-1) and IL-17 (type-17) producing proinflammatory T cells were determined 4 weeks after vaccination of 6-8 week old BALB/c female mice (n=3) with 200 μl of a water-in-oil emulsion containing 100 μg recombinant mouse α-lactalbumin and 200 μg of strain H37RA Mycobacteria tuberculosis comprising complete Freund's adjuvant (CFA). Error bars show ±SD.

T cells that mediate adaptive immune responses are divided into subsets according to their cytokine profiles. Type-1 proinflammatory T cells produce IFNγ and mediate immunity against viral and bacterial infections, whereas type-2 regulatory T cells produce Interleukin (IL)-4, IL-5, and IL-13 and mediate humoral immunity against parasitic infections. Recent studies established type-17 proinflammatory T cells which produce IL-17, as a distinct subtype that also plays a prominent role in inflammation. Both type-1 and type-17 T-cell lineages are needed to induce optimized tissue damage against self-proteins (Steinman et al., (2007) *Nat Med* 13:139-145; Luger et al., (2008) *J Exp Med* 205:799-810).

Anti-cancer vaccines are designed to stimulate the immune system to attack cancer cells. These vaccines typically include an antigen preferentially expressed by cancer cells ("tumor-associated antigens"). Most current clinical vaccine formulations induce pro-inflammatory type-1 immunity but little, if any, type-17 immunity. The present invention encompasses the insight that many current clinical vaccine formulations are not effective because they do not elicit both type-1 and type-17 immune responses. In accordance with the present invention, provided compositions induce immune responses comprising both type-1 and type-17 proinflammatory T cells. Moreover, presently disclosed compositions induce limited or no toxicity when injected into animal models, suggesting their suitability for human clinical use.

The present invention also encompasses the insight that vaccine formulations comprising an α-lactalbumin polypeptide and adjuvant components as disclosed herein may prevent and/or ameliorate breast cancers. α-lactalbumin is constitutively overexpressed in the majority of human TNBC, the most aggressive and most lethal form of breast cancer. Therefore, the presently disclosed vaccine formulations, compositions, and methods, may be useful in treating and preventing the most lethal form of breast cancers.

General

Provided herein are methods and compositions for the treatment and/or prevention of breast cancer through the induction of an immune response against α-lactalbumin. As described herein, the present disclosure involves an immunogen/adjuvant combination that induces an adaptive immune response (e.g., type-1 and type-17 T cells) for inhibiting breast cancer growth. In some aspects, the compositions comprise an α-lactalbumin polypeptide and zymosan. In some aspects, the compositions comprise an α-lactalbumin polypeptide and MONTANIDE™. In some aspects, the compositions comprise an α-lactalbumin polypeptide, zymosan, and MONTANIDE™. The α-lactalbumin in combination with zymosan and/or MONTANIDE™ of the present disclosure induce high frequencies of Type-1/Type-17 T cells associated with effective tumor immunity without inducing unresolved granulomas associated with vaccination with CFA, the "gold standard" adjuvant. Thus, vaccination with α-lactalbumin combined with zymosan and/or MONTANIDE™ provide a unique way to provide safe and effective immunity against growth of human breast cancer.

I. Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, "adjuvant" means substances, which when administered before, together with, or after administration of an antigen, accelerates, prolong and/or enhances the quality and/or strength of an immune response to the antigen in comparison to the response elicited by administration of the antigen alone.

As used herein, "anti-cancer therapy" means a therapy directed to treating, ameliorating, and/or reducing risk or progression of cancer or a cancerous condition. In some embodiments, an anti-cancer therapy comprises an anti-cancer agent, an agent that is used to treat, ameliorate, and/or reduce risk or progression of cancer or a cancerous condition.

As used herein, the term "antigen" has its ordinary meaning in the art and refers to any molecule or portion of a molecule that can, either by itself or in conjunction with an adjuvant and/or pharmaceutically acceptable carrier, generate an immune response, e.g., an antibody and/or T cell response.

As used herein, the term "administering" means providing a pharmaceutical agent or composition to a subject, and includes, but is not limited to, administering by a medical professional and self-administering.

As used herein, "biodegradable", when used in reference to a material, means those materials that, when introduced into cells, are broken down by cellular machinery (e.g., enzymatic degradation) or by hydrolysis into components that cells can reuse or dispose of without significant toxic effects on the cells. In some embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis.

The term "immune response" refers herein to any response to an antigen or antigenic determinant by the immune system. Exemplary immune responses include humoral immune responses (e.g. production of antigen-specific antibodies (neutralizing or otherwise)) and cell-mediated immune responses (e.g. lymphocyte proliferation). Type-1 proinflammatory immune responses are characterized by the production of IFNγ. Type-2 regulatory immune responses are characterized by expression of IL-4 or IL-5. Type-17 proinflammatory immune responses are characterized by expression of IL-17. In some instances, a mixed immune response can be generated. For example, in some instances a mixed Type-1/Type-17 inflammatory immune response is generated that is characterized by the expression of both IFNγ and IL-17.

As used herein, the phrase "metabolizable oil" means an oil that, when introduced into an organism, (1) can be broken down by or eliminated from the organism to a greater extent; (2) can be broken down by or eliminated from the organism more rapidly; and/or (3) results in reduced granuloma formation as compared to a reference level, such as the level of granuloma formation in a subject administered Complete Freund's Adjuvant or the level in a subject administered Incomplete Freund's Adjuvant. Thus, a "metabolizable oil," as that phrase is used herein, need not be completely metabolizable. "Reduced granuloma formation" may be characterized, for example, by one or more of: fewer granulomas formed, granulomas of reduced severity, granulomas whose severity decreases more rapidly, and granulomas that resolve (partially or completely) more quickly.

As used herein, the terms "polypeptide" and "protein" are used interchangeably and generally have their art-recognized meaning of a polymer of at least three amino acids. The term "polypeptide" can refer to polypeptides in their neutral (uncharged) forms or as salts, and either unmodified or modified, e.g., by glycosylation, side chain oxidation, or phosphorylation. The term "polypeptide" can also be used to refer to specific functional classes of polypeptides. When used to refer to a functional class of polypeptides, the term is intended to include functional fragments, variants (e.g., allelic variants), and derivatives of a reference polypeptide, as well as the full length, wild type version of the reference polypeptide. In some embodiments, a polypeptide of a certain functional class shares at least 50%, at least 55%, at least 60%, at least 65%, at least 70%, at least 75%, at least 80%, at least 85%, at least 90%, at least 95%, or at least 97.5% sequence identity at the amino acid level with the full-length version of a reference polypeptide. For example, "α-lactalbumin polypeptides," as used herein, includes α-lactalbumin as well as polypeptides having an amino acid sequence having sufficient sequence identity with the amino acid sequence of α-lactalbumin (or a portion thereof) to elicit an α-lactalbumin-specific immune response.

As used herein, "percent identity" between amino acid sequences is synonymous with "percent homology," which can be determined using the algorithm of Karlin and Altschul (*Proc. Natl. Acad. Sci. USA* 87, 2264-2268, 1990), modified by Karlin and Altschul (*Proc. Natl. Acad. Sci. USA* 90, 5873-5877, 1993). The noted algorithm is incorporated into the NBLAST and XBLAST programs of Altschul et al. (*J. Mol. Biol.* 215, 403-410, 1990). BLAST nucleotide searches are performed with the NBLAST program, score=100, wordlength=12, to obtain nucleotide sequences homologous to a polynucleotide described herein. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (*Nucleic Acids Res.* 25, 3389-3402, 1997). When utilizing BLAST and Gapped BLAST programs, the default parameters of the respective programs (e.g., XBLAST and NBLAST) are used.

The phrase "pharmaceutically acceptable carrier" as used herein means a pharmaceutically acceptable material, composition, or vehicle, such as a liquid or solid filler, diluent, excipient, thickening agent, solvent, or encapsulating material, involved in carrying or transporting the subject compound from one organ, or portion of the body, to another organ, or portion of the body. The term "carrier" encompasses both carriers that are not covalently attached and those that are covalently attached to the compounds or compositions they transport.

As used herein, the term "purified" means enrichment of a molecule, compound, or composition relative to other components normally associated with the molecule, compound, or composition in a native environment. The term "purified" does not necessarily indicate that complete purity of the molecule, compound, or composition has been achieved. In some embodiments, a "purified" molecule, compound, or composition is at least 90%, at least 95%, or at least 97.5% free of other components.

As used herein, the term "tumor-associated antigen" has its art-recognized meaning and refers to an antigen whose expression is highly correlated with a tumor cell. The tumor-associated antigen may or may not also be expressed in normal cells. In some embodiments, the tumor-associated antigen is over-expressed in tumor cells. In some embodiments, expression of the tumor-associated antigen is correlated with a particular subtype or particular subtypes of tumor cells.

As used herein, the terms "subject" and "patient" are interchangeable and refer to an organism that receives a treatment or vaccine (e.g., by being administered a composition or formulation as disclosed herein). Examples of subjects and patients include mammals, such as humans or non-human animals.

The phrases "therapeutically-effective amount" and "effective amount" as used herein means the amount of an agent that is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

The term "reference" refers to any sample, standard, or level that is used for comparison purposes. The phrases "reference standard" and "reference level" may be used interchangeably and refer to a value or number derived from a reference sample or subject. In some embodiments, the sample or subject from whom the reference level is derived is matched to a sample of a subject by at least one of the following criteria: age, weight, disease stage, and overall health.

For example, in some embodiments, a reference level is a clinical grade or score, or an average clinical grade or score.

The term "retired self-proteins" refers to self-proteins that are no longer expressed in normal aged tissues at autoimmunogenic levels. The term "retired self-antigen" refers to an antigen from a retired self-protein. In some embodiments, the retired self-antigen comprises a fragment of the retired self-protein. In some embodiments, the retired self-antigen comprises a full-length version of the retired self-protein.

The term "surfactant" as used herein has its art-recognized meaning and refers to a substance that tends to reduce the surface tension between two liquids, between a gas and a liquid, or between a liquid and a solid. In some embodiments, the surfactant is an emulsifier, a substance that stabilizes an emulsion.

II. Compositions

In one aspect, provided are compositions comprising: a carbohydrate, and a metabolizable oil, wherein (i) the composition further comprises an antigen, or (ii) the carbohydrate comprises a polysaccharide and the composition comprises a mixture of at least two polysaccharides.

In some embodiments, the antigen is a tumor-associated antigen.

In some embodiments, the carbohydrate comprises a polysaccharide and the composition comprises a mixture of at least two polysaccharides.

In some embodiments, the composition comprises a tumor-associated antigen, the carbohydrate comprises a polysaccharide, and the composition comprises a mixture of at least two polysaccharides.

In some embodiments, the composition induces an antigen-specific T cell immune response comprising at least one of (i) a type-1 proinflammatory response and (ii) a type-17 proinflammatory T cell response, when the composition is administered to a subject.

In some embodiments, the composition comprising an antigen, or further comprising an antigen, induces an antigen-specific T cell immune response comprising both a type-1 and a type-17 proinflammatory T cell response when administered to a subject.

Compositions may further comprise a surfactant, as described further herein.

A. Carbohydrates

In some embodiments, the carbohydrate comprises a polysaccharide, for example, a polysaccharide selected from the group consisting of chitin, dextran, glucan, lentanan, mannan, and combinations thereof.

In some embodiments, the composition comprises a mixture of polysaccharides, for example, a mixture comprising at least three polysaccharides.

In some embodiments, the polysaccharide each polysaccharide in the mixture is selected from the group consisting of chitin, dextran, glucan, lentanan, mannan, and combinations thereof.

In some embodiments, the polysaccharide or mixture of polysaccharides comprises a glucan, e.g., a β-glucan, such as, but not limited to 1-3 β-glucan. 12. In some embodiments, at least 50% of the carbohydrates in the composition are β-glucans.

In some embodiments, the mixture of polysaccharides comprises a mixture of chitins, glucans, and mannans.

In some embodiments, the carbohydrate binds to a pattern recognition receptor, e.g., a TLR2 and/or dectin-1.

For example, in some embodiments, the composition comprises zymosan. Zymosan is a crude cell-wall component mixture of the baker's yeast extracts from *Saccharomyces cerevisiae*, composed mainly of β-glucans (50-57%), mannans, and chitins. The US Food and Drug Administration (FDA) has given these β-glucans derived from yeast extract a GRAS ("Generally Recognized as Safe") rating. Yeast zymosan serves as a rich source of β (1,3) glucan. Yeast-derived β (1,3) glucan appears to stimulate the immune system, in part, by activating the innate immune system as part of the body's basic defense against fungal infection (Huang et al., (2013) Clin Vaccine Immunol 20:1585-1591). Yeast β (1,3) glucan is a polysaccharide composed primarily of β (1-3)-linked glucose molecules with periodic β (1-3) branches linked via β (1-6) linkages and is more formally known as poly-(1-6)-β-glucopyranosyl-(1-3)-β-D-glucopyranose.

B. Metabolizable Oils

As used herein, the phrase "metabolizable oil" means an oil that, when introduced into an organism, (1) can be broken down by or eliminated from the organism to a greater extent; (2) can be broken down by or eliminated from the organism more rapidly; and/or (3) results in reduced granuloma formation as compared to Incomplete Freund's Adjuvant. Thus, a "metabolizable oil," as that phrase is used herein, need not be completely metabolizable. "Reduced granuloma formation" may be characterized, for example, by one or more of: fewer granulomas formed, granulomas of reduced severity, and granulomas that resolve more quickly.

In some embodiments, the metabolizable oil comprises mineral oil.

In some embodiments, the metabolizable oil comprises a purified oil, e.g., purified mineral oil (such as, but not limited to DRAKEOL™ 6 VR).

In some embodiments, the metabolizable oil comprises a biodegradable oil. Non-limiting examples of biodegradable oils include isopropyl myristate, squalene oil (e.g., MF59), squalane oil, a vegetable oil, or a combination thereof. In some embodiments, the biodegradable oil is a vegetable oil, such as, for example, almond oil, castor oil, chaulmoogra oil, coconut oil, corn oil, cottonseed oil, olive oil, peanut oil, persic oil, safflower oil, soya bean oil, or a combination thereof.

In some embodiments, the metabolizable oil comprises fish oil.

In certain embodiments, the metabolizable oil is a pharmaceutical grade oil.

C. Surfactants/Emulsions

In some embodiments, a provided composition comprises one or more surfactants. Non-limiting examples of suitable surfactants include mannide monooleate, isomannide monooleate, and combinations thereof. In some embodiments, the composition comprises mannide monooleate.

In some embodiments, provided compositions comprise MONTANIDE™, e.g., a MONTANIDE™ ISA series adjuvant, that comprises a metabolizable oil.

MONTANIDE™ ISA (ISA=Incomplete Seppic Adjuvant) adjuvants (Seppic SA, Paris, France) are a group of oil/surfactant-based adjuvants in which different surfactants are combined with a non-metabolizable mineral oil, a metabolizable oil, or a mixture of the two. They are typically prepared for use as an emulsion with an aqueous antigen solution. The various MONTANIDE™ ISA group of adjuvants are used as water-in-oil emulsions, oil-in-water emulsions, or water-in-oil-in-water emulsions.

In some embodiments, the composition comprises MONTANIDE™ ISA 51, MONTANIDE™ ISA 51 VG, or any bioequivalent adjuvant derived therefrom (for example, by replacing the oleic acid isolated from olives by that isolated from another source or a synthetic one). MONTANIDE™ ISA 51 is a mixture of a highly purified mineral oil (DRAKEOL™ 6 VR) and a surfactant (mannide monooleate). MONTANIDE™ ISA 51 VG is a similar composition in which the oleic acid is obtained from olives rather than from an animal source In some embodiments, provided compositions are emulsions of water and oil, e.g., water-in-oil emulsions. Methods of creating water-in-oil (w/o) emulsions are well known in the art. A water-in-oil emulsion can be obtained by any of a variety of protocols, such as protocols using any of a variety of devices such as high shear mixers, vortex mixers, and syringes with or without connectors (e.g., T- or I-connectors). In some embodiments, provided compositions comprise adjuvant (such as a MONTANIDE™ adjuvant) that creates a depot effect, that is, an adjuvant that causes an antigen in the same composition to be slowly released in the body, thus prolonging the exposure of immune cells to the antigen.

D. Antigens

Generally, any molecule or portion of a molecule against which an immune response is desired may be used as an antigen. Antigens may comprise any one of, but are not limited to, peptides, polypeptides, proteins, cells (or component thereof), live-attenuated pathogens (or component thereof), and heat-killed pathogens (or component thereof).

In some embodiments, antigens are non-self antigens, that is, they are foreign to the organism to which a composition comprising an antigen is intended to be administered.

In some embodiments, antigens are self-antigens in that they are or were expressed in at least some cells in the organism to which organism to which a composition comprising an antigen is intended to be administered. In some embodiments, antigens are retired self-proteins in that they were once expressed in an organism but no longer expressed at autoimmunogenic levels in non-malignant mature cells.

In some embodiments, antigens are tumor-associated antigens.

In some embodiments, provided compositions or formulations comprise a mixture of different antigens.

Antigens may comprise one or more modifications. For example, one or more modifications that affect processing, cellular uptake, immunogenicity, and/or stability (e.g., within a peptide/MHC complex) of an antigen or fragment thereof may be used.

In some embodiments, antigens comprise polypeptide antigens. Polypeptide antigens may be any of a variety of lengths, and their sequences may or may not correspond to sequences of naturally occurring proteins. For example, in some embodiments, a full-length or nearly full-length protein may be used as a polypeptide antigen. In some embodiments, antigens or antigen mixtures comprise one or more fragments or variants of a protein.

α-Lactalbumin Polypeptides

In some embodiments, the antigen comprises an α-lactalbumin polypeptide or an immunogenic fragment thereof. In some embodiments, the antigen comprises multiple (e.g., at least 2, 3, 4, 5, 6, 7, 8, 9, or 10) different α-lactalbumin polypeptides or fragments. In some embodiments, provided compositions comprise a nucleic acid encoding an α-lactalbumin polypeptide instead of or in addition to the α-lactalbumin polypeptide.

The LALBA gene encodes α-lactalbumin, a principal protein of milk. α-lactalbumin forms the regulatory subunit of the lactose synthase (LS) heterodimer, and β 1,4-galactosyltransferase (β4Gal-T1) forms the catalytic component. Together, these proteins enable LS to produce lactose by transferring galactose moieties to glucose. As a monomer, α-lactalbumin strongly binds calcium and zinc ions and may possess bactericidal or antitumor activity. The human LALBA gene contains 5 exons.

Human α-lactalbumin precursor protein has 142 amino acids and a molecular mass of 14,178 Da, and human α-lactalbumin has 123 amino acids. In some embodiments, the α-lactalbumin polypeptide has 123 amino acids. The term "α-lactalbumin polypeptide" is intended to include fragments, variants (e.g., allelic variants), and derivatives thereof. Representative human α-lactalbumin cDNA and human α-lactalbumin protein sequences are well known in the art and are publicly available from the National Center for Biotechnology Information (NCBI). For example, at least one human UBE2D3 isoform are known. Human UBE2D3 isoform (NP_002280.1) is encodable by the transcript variant (NM 002289.2). Nucleic acid and polypeptide sequences of α-lactalbumin orthologs in organisms other than humans are well known and include, for example, chimpanzee α-lactalbumin (NM_016924811.2 and XP_016780300.1), monkey α-lactalbumin (XM_001102116.2 and XP_001102116.1), dog α-lactalbumin (NM_001003129.1 and NP_001003129.1), cattle α-lactalbumin (NM_174378.2 and NP_776803.1), mouse α-lactalbumin (NM_010679.1 and NP_034809.1), and rat α-lactalbumin (NM_012594.1 and NP_036726.1). Each of the above mRNA and protein sequences are hereby incorporated by reference. Representative sequences of α-lactalbumin orthologs are presented below in Table 1.

TABLE 1

```
SEQ ID NO: 1 Human LALBA Amino Acid Precursor Sequence (NP_002280.1)
     1   mrffvplflv gilfpailak qftkcelsql lkdidgyggi alpelictmf htsgydtqai 61   vennesteyg lfqisnklwc kssqvpqsrn icdiscdkfl ddditddimc akkildikgi 121   dywlahkalc tekleqwlce kl SEQ ID NO: 2 Human LALBA cDNA Sequence (NM_002289.2; CDS: 27-455)
     1   atttcaggtt cttgggggta gccaaaatga ggttctttgt ccctctgttc ctggtgggca 61   tcctgttccc tgccatcctg gccaagcaat tcacaaaatg tgagctgtcc cagctgctga 121   aagacataga tggttatgga ggcatcgctt tgcctgaatt gatctgtacc atgtttcaca 181   ccagtggtta tgacacacaa gccatagttg aaaacaatga agcacggaa tatggactct 241   tccagatcag taataagctt tggtgcaaga gcagccaggt ccctcagtca aggaacatct 301   gtgacatctc ctgtgacaag ttcctggatg atgacattac tgatgacata atgtgtgcca 361   agaagatcct ggatattaaa ggaattgact actggttggc ccataaagcc ctctgcactg 421   agaagctgga acagtggctt tgtgagaagt tgtgagtgtc tgctgtcctt ggcaccctg 481   cccactccac actcctggaa tacctcttcc ctaatgccac ctcagtttgt ttctttctgt 541   tcccccaaag cttatctgtc tctgagcctt gggcctgta gtgacatcac cgaattcttg 601   aagactattt tccagggatg cctgagtggt gcactgagct ctagacccctt actcagtgcc 661   ttcgatggca ctttcactac agcacagatt tcacctctgt cttgaataaa ggtcccactt 721   tgaagtcaaa aaaaaaaaa aa SEQ ID NO: 3 Mouse LALBA Amino Acid Sequence (NP_034809.1)
     1   mmhfvplflv cilslpafga teltkckvsh aikdidgyqg isllewacvl fhtsgydtqa 61   vvndngstey glfqisdrfw ckssefpese nicgiscdkl lddeldddia cakkilaikg 121   idywkaykpm csekleqwrc ekp SEQ ID NO: 4 Mouse LALBA cDNA Sequence (NM_010679.1; CDS:13-444)
     1   ggagcagtca aaatgatgca tttcgttcct ttgttcctgg tgtgtatttt gtcgttgcct 61   gcctttcaag ccacagagct tacaaaatgc aaggtgtccc atgccattaa agacatagat 121   ggctatcaag gcatctcttt gcttgaatgg gcctgtgttt tatttcatac cagtggctac 181   gacacacaag ctgttgtcaa cgacaacggc agcacagagt acggactctt ccagatcagt 241   gacagatttt ggtgtaaaag tagtgagttc cccgagtcgg agaacatctg tggcatctcc 301   tgtgacaagt tattggatga cgagttggat gatgacatag cgtgtgccaa gaagatcctg 361   gctatcaaag gaatcgacta ctggaaagcc tacaagccca tgtgctctga gaagcttgaa 421   cagtggcgtt gtgagaagcc ctgagccccc cccccccccc ccccgtcct tgctgctcct
```

TABLE 1-continued

```
481    gccccgtggt caggaatgcc tcttccctaa ggctacctca gcttggctct tgctattcct 541    gtgaagatga tctgcctctg agccttgtac cctgtagtga caccaccgga ctctagagga 601    cttttttttc cctatgggag tgtgactggc gcactggact gcaaaccctt gcttagtgac 661    ggcgagggtc tcgatgggg ttttacaaaa tcgagagagc cctctcctgt cccaaataaa 721    gggccagact tga SEQ ID NO: 5 Human LALBA Amino Acid Sequence
  1    kqftkcelsq llkdidgygg ialpelictm fhtsgydtqa ivennestey 61    glfqisnklw ckssqvpqsr nicdiscdkf lddditddim cakkildikg 121    idywlahkal ctekleqwlc ekl
```

*Included in Table 1 are RNA nucleic acid molecules (e.g., thymines replaced with uridines), nucleic acid molecules encoding orthologs of LALBA, as well as DNA or RNA nucleic acid sequences comprising a nucleic acid sequence haying at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof Such nucleic acid molecules can have a function of the full-length nucleic acid as described further herein.
*Included in Table 1 are orthologs of LALBA, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

In some embodiments, provided herein are α-lactalbumin polypeptides and/or nucleic acids encoding α-lactalbumin polypeptides. α-lactalbumin polypeptides are polypeptides that include an amino acid sequence that have sufficient sequence identity with the amino acid sequence of α-lactalbumin or a portion thereof to elicit an α-lactalbumin-specific immune response.

In some embodiments, provided are fusion polypeptides comprising an α-lactalbumin polypeptide and a heterologous polypeptide.

In certain embodiments, the α-lactalbumin polypeptide has an amino acid sequence that comprises at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids of an α-lactalbumin amino acid sequence set forth in Table 1 (e.g., SEQ ID NO: 1, 3, or 5). In some embodiments, the consecutive amino acids are identical to an α-lactalbumin amino acid sequence set forth in Table 1.

In certain embodiments, the α-lactalbumin polypeptide has an amino acid sequence that consists essentially of at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids of an α-lactalbumin amino acid sequence set forth in Table 1. In some embodiments, the consecutive amino acids are identical to an amino acid sequence of α-lactalbumin amino acid sequence set forth in Table 1.

In certain embodiments, the α-lactalbumin polypeptide has an amino acid sequence that consists of at least 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids of an α-lactalbumin amino acid sequence. In some embodiments, the consecutive amino acids are identical to an α-lactalbumin amino acid sequence set forth in Table 1.

In some embodiments, the α-lactalbumin polypeptide has an amino acid sequence that comprises 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids that are at least 70%, 75%, 80%, 85%, 90%, 91%, 92%, 93%, 94%, 95%, 96%, 97%, 98% or 99% identical to an α-lactalbumin amino acid sequence set forth in Table 1. In some embodiments, the consecutive amino acids are identical to an α-lactalbumin amino acid sequence set forth in Table 1.

In some embodiments, the α-lactalbumin polypeptide has an amino acid sequence that comprises at least 8 consecutive amino acids of SEQ ID NO: 5.

In some embodiments, the α-lactalbumin polypeptide has an amino acid sequence that consists essentially of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids that are at least 70%, 75%, 80%, 85%, 90%, 91%, 92%, 93%, 94%, 95%, 96%, 97%, 98% or 99% identical to an α-lactalbumin amino acid sequence set forth in Table 1. In some embodiments, the consecutive amino acids are identical to an α-lactalbumin amino acid sequence set forth in Table 1.

In some embodiments, the α-lactalbumin polypeptide has an amino acid sequence that consists of 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, or 140 consecutive amino acids that are at least 70%, 75%, 80%, 85%, 90%, 91%, 92%, 93%, 94%, 95%, 96%, 97%, 98% or 99% identical to an α-lactalbumin amino acid sequence set forth in Table 1. In some embodiments, the consecutive amino acids are identical to an α-lactalbumin amino acid sequence set forth in Table 1.

As is well known to those skilled in the art, polypeptides having substantial sequence similarities can cause identical or very similar immune reactions in a host organism. Accordingly, in some embodiments, an α-lactalbumin polypeptide that is a derivative, equivalent, variant, fragment, or mutant of α-lactalbumin can also be suitable for use in the methods and compositions provided herein.

In some embodiments, provided α-lactalbumin polypeptides are functional equivalents in that they have an amino acid sequence that is altered relative to the sequence of α-lactalbumin polypeptide (for example, by conservative substitution), yet still elicit immune responses. As used herein, the term "conservative substitution" denotes the replacement of an amino acid residue by another, biologically similar residue. It is well known in the art that the amino acids within the same conservative group can typically substitute for one another without substantially affecting the function or immunogenicity of a protein.

In some embodiments, provided herein are nucleic acids, such as DNA molecules, encoding α-lactalbumin polypeptides described herein. In some embodiments, provided are compositions comprising an expression vector comprising an open reading frame encoding an α-lactalbumin polypeptide. In some embodiments, the α-lactalbumin nucleic acid includes regulatory elements that facilitate expression of the open reading frame. Such elements can include, for example, one or more of a promoter, an initiation codon, a stop codon, and a polyadenylation signal. In addition, one or more enhancers can be included. These elements can be operably linked to a sequence that encodes the α-lactalbumin polypeptide.

Examples of promoters include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metallothionein. Examples of suitable polyadenylation signals include, but are not limited to, SV40 polyadenylation signals and LTR polyadenylation signals.

Non-limiting examples of enhancers or enhancers/promoters include, for example, enhancers from human actin, human myosin, human hemoglobin, human muscle creatine, and viral enhancers, such as those from CMV, RSV and EBV.

In some embodiments, provided nucleic acids are incorporated in a carrier or delivery vector. Useful delivery vectors include but are not limited to biodegradable microcapsules, immuno-stimulating complexes (ISCOMs), liposomes, and genetically engineered attenuated live carriers such as viruses or bacteria.

In some embodiments, the vector is a viral vector, non-limiting examples of which include lentiviruses, retroviruses, herpes viruses, adenoviruses, adeno-associated viruses, vaccinia viruses, baculoviruses, Fowl pox viruses, AV-pox viruses, modified vaccinia Ankara (MVA) viruses, and other recombinant viruses. For example, a vaccinia virus vector can be used to infect dendritic cells.

F. Formulations and Pharmaceutical Compositions

In some embodiments, the antigen and the carbohydrate are present in a ratio of from about 10:1 to about 1:10 (w/w), for example, from about 5:1 to about 1:5 (w/w), from about 4:1 to 1:4 (w/w), from about 3:1 to about 1:3 (w/w), or from about 1:2 to about 2:1 (w/w). In some embodiments, the antigen and the carbohydrate are present in a ratio of about 1:1 (w/w).

In some embodiments, provided compositions comprise an antigen, zymosan, and MONTANIDE™. In some such embodiments, the antigen is a polypeptide antigen.

For example, compositions that may be suitable for treatment and/or prevention of breast cancer may comprise an α-lactalbumin polypeptide, zymosan, and MONTANIDE™, wherein the α-lactalbumin polypeptide comprises an amino acid sequence that is at least 80%, 85%, 90%, or 95% identical to the amino acid sequence of SEQ ID NO: 5. In some embodiments, the α-lactalbumin polypeptide comprises an amino acid sequence that is 100% identical to the amino acid sequence of SEQ ID NO: 5.

In some embodiments, provided compositions are formulated as an emulsion of water and oil, e.g., a water-in-oil emulsion.

In some embodiments, provided are formulations comprising a water-in-oil emulsion of an antigen, zymosan, and MONTANIDE™. In some such embodiments, the antigen is a polypeptide antigen.

For example, in some embodiments, the formulation comprises a water-in-oil emulsion of α-lactalbumin polypeptide, zymosan, and MONTANIDE™, wherein the α-lactalbumin polypeptide and zymosan are present in the formulation at a ratio of between about 1:5 (w/w) and 5:1) (w/w), and wherein the α-lactalbumin polypeptide comprises an amino acid sequence that is at least 80%, 85%, 90%, or 95% identical to the amino acid sequence of SEQ ID NO: 5. In some such embodiments, the α-lactalbumin polypeptide comprises an amino acid sequence that is 100% identical to the amino acid sequence of SEQ ID NO: 5.

In some aspects, provided herein are pharmaceutical compositions (e.g., vaccine compositions). For example, in some embodiments, provided compositions further comprise a pharmaceutically acceptable carrier.

In some embodiments, compositions further comprise an antibiotic.

Pharmaceutical compositions disclosed herein may be specially formulated for administration in solid or liquid form, including those adapted for the following: (1) oral administration, for example, drenches (aqueous or nonaqueous solutions or suspensions), tablets (e.g., those targeted for buccal, sublingual, or systemic absorption), boluses, powders, granules, or pastes (e.g., for application to the tongue); or (2) parenteral administration, for example, by subcutaneous, intramuscular, intravenous, or epidural injection. Non-limiting examples of formulations suitable for parenteral administration include sterile solutions, sterile suspensions, and sustained-release formulations.

Methods of preparing these formulations or compositions may include a step of bringing into association an antigen with the carbohydrate, metabolizable oil, pharmaceutically acceptable carrier, and, optionally, one or more accessory ingredients. In general, formulations may be prepared by uniformly and intimately bringing into association one or more composition components described herein with liquid pharmaceutically acceptable carriers, finely divided solid pharmaceutically acceptable carriers, or both, and then, if necessary, shaping the product.

Pharmaceutical compositions suitable for parenteral administration may be provided as pharmaceutically acceptable sterile isotonic aqueous or nonaqueous solutions, dispersions, suspensions or emulsions. Alternatively or additionally, pharmaceutical compositions for parenteral administration may be provided as sterile powders, which may be reconstituted into sterile injectable solutions or dispersions just prior to use. Such injectable solutions may contain one or more agents that render the formulation isotonic with the blood of the intended recipient, one or more suspending agents, and/or one or more thickening agents. For example, injectable solutions may comprise one or more of sugars, alcohols, antioxidants, buffers, bacteriostats, and solutes.

Examples of suitable aqueous and nonaqueous pharmaceutically acceptable carriers include, but are not limited to, water, ethanol, polyols (such as glycerol, propylene glycol, polyethylene glycol, and the like), and suitable mixtures thereof; vegetable oils, such as olive oil; and injectable organic esters, such as ethyl oleate. Proper fluidity can be maintained, for example, by the use of coating materials (such as lecithin), by the maintenance of the required particle size in the case of dispersions, and by the use of surfactants.

Pharmaceutical compositions disclosed herein may be formulated as emulsions. For examples, provided are vaccine compositions formulated as emulsions, which provide an alternative to aluminum-based vaccines. Emulsion formulations may be prepared by emulsifying antigens dissolved in an aqueous buffer with an oil, such as any metabolizable oil, as further described herein. Emulsion formulations may form a short-lived depot to facilitate vaccine phagocytosis by innate immune cells, which results in an immune response (Leenaars, Koedam et al. 1998). The oils used in such emulsions can impart unique immune stimulation and result in stronger immune responses than can vaccines comprising alum adjuvants (De Gregorio, Caproni et al. 2013).

In some embodiments, the present disclosure provides a pharmaceutical composition comprising an emulsion, e.g., a water-in-oil emulsion, comprising an antigen and a metabolizable oil, as described herein. For example, in some embodiments, the present disclosure provides a pharmaceutical composition comprising α-lactalbumin polypeptides, zymosan, and a metabolizable oil.

In certain embodiments, the present disclosure provides a pharmaceutical composition comprising about 40-60% v/v of aqueous phase antigen emulsified with about 40-60% v/v of a metabolizable oil (optionally in which a carbohydrate, as described further herein, is mixed). For example, the pharmaceutical composition may comprise about 0.1-25 mg/mL (e.g., 0.5-5 mg/mL) antigen in about 50% v/v of a metabolizable oil/carbohydrate composition.

In some embodiments, an emulsion of the pharmaceutical composition disclosed herein is formed by mixing aqueous phase antigen with a metabolizable oil at a ratio of from about 1.5:1 to about 1:1.5, such as about 1.5:1, about 1.4:1, about 1.3:1, about 1.2:1, about 1.1:1, about 1:1, about 1:1.1, about 1:1.2, about 1:1.3, about 1:1.4, or about 1:1.5, or any value in between. In some embodiments, a carbohydrate is suspended in the metabolizable oil before forming emulsions. In some embodiments, zymosan is suspended in the metabolizable oil before forming emulsions.

Pharmaceutical compositions disclosed herein may be formulated into pharmaceutically acceptable dosage forms by conventional methods known to those of skill in the art.

Metabolizable oils and/or the carbohydrates in provided pharmaceutical compositions may, in some embodiments, act as an adjuvant that increases the immunogenicity of the pharmaceutical composition.

In some embodiments, an additional physiologically acceptable adjuvant is employed. Such a an additional adjuvant may be used or included in any of a number of ways, including, but not limited to, (i) admixed to other components in a pharmaceutical composition as provided herein after reconstitution of antigens (e.g., polypeptide antigens) and optional emulsification with a metabolizable oil as defined above, (ii) part of a reconstituted antigen-containing composition as provided herein, (iii) physically linked to antigen(s) to be reconstituted; and (iv) administered separately to the subject. The additional adjuvant can, for example, slow release of antigen (e.g., the additional adjuvant can be a liposome) and/or it can be an adjuvant that is immunogenic in its own right, thereby functioning synergistically with antigens (i.e., antigens present in a provided composition).

For example, the additional adjuvant can be a known adjuvant or other substance that promotes antigen uptake, recruits immune system cells to the site of administration, and/or facilitates the immune activation of responding lymphoid cells. Examples of suitable additional adjuvants include, but are not limited to, immunomodulatory molecules (e.g., cytokines), oil and water emulsions, aluminum hydroxide, glucan, dextran sulfate, iron oxide, sodium alginate, Bacto-Adjuvant, synthetic polymers such as poly amino acids and co-polymers of amino acids, saponin, paraffin oil, and muramyl dipeptide. In some embodiments, the additional adjuvant is Adjuvant 65, α-GalCer, aluminum phosphate, aluminum hydroxide, calcium phosphate, β-Glucan Peptide, CpG DNA, GM-CSF, GPI-0100, IFA, IFN-γ, IL-17, lipid A, lipopolysaccharide, Lipovant, MONTANIDE™, N-acetyl-muramyl-L-alanyl-D-isoglutamine, Pam3CSK4, quil A, trehalose dimycolate, or zymosan. In some embodiments, the additional adjuvant induces a mixed type 1/type 17 immune response.

In some embodiments, the additional adjuvant is an immunomodulatory molecule that enhances immune responses. For example, the immunomodulatory molecule can be a cytokine, chemokine, or immunostimulatory agent, recombinant versions of any of the foregoing, or nucleic acids encoding any of the foregoing.

Examples of immunomodulatory cytokines include, but are not limited to, interferons (e.g., IFNα, IFNβ and IFNγ), interleukins (e.g., IL-1, IL-2, IL-3, IL-4, IL-5, IL-6, IL-7, IL-8, IL-9, IL-10, IL-12, IL-17 and IL-20), tumor necrosis factors (e.g., TNFα and TNFβ), erythropoietin (EPO), FLT-3 ligand, gIp10, TCA-3, MCP-1, MIF, MIP-1α, Rantes, macrophage colony stimulating factor (M-CSF), granulocyte colony stimulating factor (G-CSF), and granulocyte-macrophage colony stimulating factor (GM-CSF), as well as functional fragments of any of the foregoing.

In some embodiments, provided compositions comprise an immunomodulatory chemokine that binds to a chemokine receptor, e.g., a CXC, CC, C, or CX3C chemokine receptor. Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, 1309, IL-8, Gcp-2 Gro-α, Gro-β, Gro-γ, Nap-2, Ena-78, Gcp-2, Ip-10, Mig, I-Tac, Sdf-1, and Bca-1 (B1c), as well as functional fragments of any of the foregoing.

G. Additional Agents

In certain embodiments, compositions provided herein also comprise one or more additional agents such as, but not limited to, anti-cancer agents (e.g., chemotherapeutics), immunotherapeutic, immunomodulatory and/or anti-angiogenic agents.

In some embodiments, compositions comprise an additional anti-cancer agent. In some embodiments, the anti-cancer agent is selected from the group consisting of bevacizumab, bleomycin, carboplatin, cisplatin, cyclophosphamide, docetaxel, doxorubicin, etoposide, gemcitabine, letrozole, olaparib, tamoxifen, topotecan, trabectedin, a CTLA4 antibody, a PD-1 antibody, a PD-L1 antibody, and a TGFβ antibody.

In some embodiments, the additional agent is a naturally occurring or synthetic anti-cancer agent, for example, an anti-cancer agent as described in "Cancer Chemotherapeutic Agents," American Chemical Society, 1995, W. O. Foye Ed.

In some embodiments, the anti-cancer agent comprises a small molecule.

In some embodiments, the anti-cancer agent is a receptor antagonist or blocker. In some embodiments, the chemotherapeutic agent is selected from the group consisting of VEGF receptor antagonists (such as, for example, vatalanib (PTK-787/ZK222584), SU-5416, SU-6668, SU-11248, SU-14813, AZD-6474, AZD-2171, CP-547632, CEP-7055, AG-013736, IM-842 or GW-786034), VEGFtrap, EGFR and/or HER2 antagonists (such as, for example, gefitinib, erlotinib, CI-1033, GW-2016, herceptin, iressa (ZD-1839), tarceva (OSI-774), PKI-166, EKB-569, or HKI-272), integrin receptor antagonists, and protein kinase receptor antagonists (e.g., atrasentan). In some embodiments, the chemotherapeutic agent inhibits expression of HER2.

In some embodiments, the anti-cancer agent comprises an antagonist of a protein kinase, for example, an antagonist of mitogen-activated protein kinase (e.g., BAY-43-9006 or BAY-57-9006) or imatinib.

In some embodiments, the anti-cancer agent comprises a tubulin-binding agent.

In some embodiments, the anti-cancer agent comprises an antibody. For example, chemotherapeutic antibodies include, but are not limited to, antibodies directed against cytokines (e.g., TGFβ), antibodies targeting surface molecules of cancer cells, and antibodies targeting growth factors or their receptors. Non-limiting examples of antibody chemotherapeutics include alemtuzumab, apolizumab, bevacizumab, daclizumab, cetuximab, ibritumomab, mitumomab, matuzumab, oregovomab, rituximab, vitaxin (a vitronectic receptor antibody), DC101 (a VEGFR2 antibody), ID09C3 (an MHC class II monoclonal antibody), and IMC-1C11 (a kinase insert domain receptor antibody).

In some embodiments, the anti-cancer agent comprises a cell cycle inhibitor.

In some embodiments, the anti-cancer agent comprises a cytokine inhibitor.

In some embodiments, the anti-cancer agent comprises a hypoxia-selective cytotoxin.

In some embodiments, the anti-cancer agent comprises a TNFα inhibitor, e.g., etanercept.

In some embodiments, the anti-cancer agent comprises an interferon, e.g., interferon β.

In some embodiments, the anti-cancer agent comprises an interleukin, e.g., IL-10 or IL-12.

In some embodiments, the anti-cancer agent comprises an immunomodulator, e.g., lenalidomide or thalidomide.

In some embodiments, the anti-cancer agent comprises an immune checkpoint inhibitor. In some embodiments, the immune checkpoint inhibitor is an inhibitor of CTLA4, such as a CTLA4 antibody (e.g., ipilimumab (BMS), tremelimumab (AstraZeneca) and/or KAHR-102 (Kahr Medical)). In some embodiments, the immune checkpoint inhibitor is an inhibitor of PD-1, such as a PD-1 antibody (e.g., nivolumab (BMS), pembrolizumab/lambrolizumab (Merck), pidilizumab (Curetech), AMP-224 (GSK), AMP-514 (AstraZeneca), STI-A1110 (Sorrento) and/or TSR-042 (Tesaro). In some embodiments, the immune checkpoint inhibitor is an inhibitor of PD-L1 and/or PD-L2, such as a PD-L1 and/or a PD-L2 antibody (e.g., RG-7446 (Roche), BMS-936559 (BMS), MEDI-4736 (AstraZeneca), MSB-0020718C (Merck), AUR-012 (Pierre Fabre Med), STI-A1010 (Sorrento)). In some embodiments, the anti-cancer agent comprises a leukotriene antagonist.

In some embodiments, the anti-cancer agent comprises a DNA alkylating agent, such as, for example, a nitrogen mustard or derivative thereof (e.g., bendamustine, chlorambucil, chlormethine (mechlorethamine), oxazaphosphorines (e.g., cyclophosphamide, ifosfamide, and trofosfamide), melphalan, nitromin, uramustine), a nitrosourea (e.g., carmustine, lomustine, or streptozocin), an alkylsulfonate (e.g., busulfan), an ethyleneimine (aziridine) (e.g., thiotepa or hexamethylmelamine), a metal salt (e.g., carboplatin, cisplatin, or oxaliplatin), or a hydrazine (e.g., altretamine, procarbazine, dacarbazine, or temozolomide).

In some embodiments, the anti-cancer agent comprises a platinum compound such as, for example, cisplatin, oxaliplatin, carboplatin, satraplatin, tetraplatin, or iproplatin.

In some embodiments, the anti-cancer agent comprises a DNA intercalator, e.g., an anthracycline such as, for example, daunorubicin, doxorubicin (adriamycin), liposomal doxorubicin (doxil), epirubicin, or idarubicin.

In some embodiments, the anti-cancer agent comprises a DNA minor-groove binding compound.

In some embodiments, the anti-cancer agent comprises a DNA cross-linking agent.

In some embodiments, the anti-cancer agent comprises an antimetabolite such as, for example, a pyrimidine or purine analogue or antagonist, or a nucleoside diphosphate reductase inhibitor. Non-limiting examples of antimetabolites include cytarabine, 5-fluorouracile (5-FU), pemetrexed, tegafur/uracil, uracil mustard, floxuridine, fludarabine, gemcitabine, capecitabine, mercaptopurine, cladribine, thioguanine, methotrexate, pentostatin, or hydroxyurea.

In some embodiments, the anti-cancer agent comprises an inhibitor of DNA transcription, RNA translation, or protein expression. Non-limiting examples of DNA transcription inhibitors include topoisomerase I or II inhibitors (e.g., camptothecin, irinotecan, topotecan, epipodophyllotoxin, etoposide, teniposide, or tricyclic carboxmide-based agents) and inhibitors of transcription factor complexes (such as, for example, inhibitors of the ESX/DRIP130/Sur-2 complex).

In some embodiments, the anti-cancer agent comprises a proteasome inhibitor such as, for example, bortezomib.

In some embodiments, the anti-cancer agent comprises an enzyme, e.g., asparaginase or pegylated asparaginase (pegaspargase).

In some embodiments, the anti-cancer agent comprises an oligonucleotide or polynucleotide.

In some embodiments, the anti-cancer c agent comprises an histone deacetylase inhibitor such as, for example, SAHA, MD-275, trichostatin A, CBHA, LAQ824, or valproic acid.

In some embodiments, the chemotherapeutic agent comprises a chemical radiation sensitizers or protector.

In some embodiments, the anti-cancer agent comprises an inhibitor of an oncogene, e.g., a P53 or Rb inhibitor.

In some embodiments, the anti-cancer agent comprises a plant-derived agent such as a taxane (e.g., paclitaxel or docetaxel), a vinca alkaloid (e.g., navelbine, vinblastin, vincristin, vindesine or vinorelbine), or a tropical alkaloid (e.g., colchicine or a derivative thereof).

In some embodiments, the anti-cancer agent comprises quinazoline or a derivative thereof, such as, for example, afatanib, erlotinib, gefitinib, or lapatinib.

In some embodiments, the anti-cancer agent comprises an antimitotic agent, for example, antimitotic peptides (e.g., phomopsin and dolastatin), antimitotic carbamate derivatives (e.g., combretastatin (A4) or amphetinile).

In some embodiments, the anti-cancer agent comprises a steganacin.

In some embodiments, the anti-cancer agent comprises a hormone blocker, e.g., anti-androgens, anti-estrogens, gonadotropin-releasing hormone (GNrH) antagonists (e.g., abarelix), GNrH analogues, and aromatase inhibitors. Non-limiting examples of such anti-androgens include anandron, bicalutamide, casodex, cyproterone acetate, flutamide, mitotane, and nilutamide. Non-limiting examples of anti-estrogens include droloxifene, raloxifene, tamoxifen, trioxifene, and zindoxifene. Non-limiting examples of GNrH analogues include leuprorelin (leuprolide), buserelin, goserelin and triptorelin. Non-limiting examples of aromatase inhibitors include aminogluthetimide, anastrozole, fadrozole, formestane or letrozole, and testalactone. Additional examples of hormone blockers include finasteride.

In some embodiments, the anti-cancer agent is a hormone or a derivative thereof, e.g., an estrogen (e.g., estramustine (T-66), 17-β-estra-diol (including derivatives ICI 164,384 or ICI 182,780), a gestagen, or a progestin (e.g., megestrol).

In some embodiments, the anti-cancer agent comprises a piperazine derivative, e.g., piprobroman.

In some embodiments, the anti-cancer agent comprises a glutathione analog, e.g., TLK-286.

In some embodiments, the anti-cancer agent comprises a biological response modifier, e.g., aldesleukin or denileukin diftitox.

In some embodiments, the anti-cancer agent comprises a matrix metalloprotease inhibitor, e.g., marimastat, TIMP-1, or TIMP-2.

In some embodiments, the anti-cancer agent comprises a complex of rare earth elements, e.g., lanthanide complexes.

In some embodiments, the anti-cancer agent comprises a metal having anti-cancer effects, e.g., zinc.

In some embodiments, the anti-cancer agent comprises a photo-chemically activated drug, e.g., porfimer, photofrin, a benzoporphyrin derivative, a pheophorbide derivative, merocyanine 540 (MC-540) or tin etioporpurin.

In some embodiments, the anti-cancer agent comprises an agent used in photo-chemotherapeutic therapy, e.g., psoralens, which are used with ultraviolet therapy.

In some embodiments, the anti-cancer agent comprises a nitroaromatic compound, e.g., RSU-1069, RB-6145, or CB-1954. In some embodiments, the chemotherapeutic agent comprises a nitroxyl or N-oxide, e.g., such as SR-4233.

In some embodiments, the anti-cancer agent comprises an anti-sense RNA or DNA, e.g., oblimersen.

In some embodiments, the anti-cancer agent comprises an halogenated pyrimidine analogue, e.g., bromodeoxyuridine or iododeoxyuridine.

In some embodiments, the additional agent comprises an angiogenesis inhibitor such as, for example, DC-101, neovastat, tetrathiomolybdate, a thymidine-phosphorylase inhibitor, or TNP-470.

In some embodiments, the additional agent comprises an antibiotic (including macrolides), antifungal, or antiparasitic agent, which may or may not have an anti-cancer effect. Non-limiting examples of antibiotics that may be used as additional agents include acridine, actinomycin, amsacrine, ansamitocin, anthramycin, bleomycin, chloromycin, dactinomycin, distamycin, duocarmycin, geldanamycin, ketoconazole, liblomycin, maytansine, mithramycin, mitomycin, mitoxantone, netropsin, a nitroimidazole (e.g., benznidazole, metronidazole, misonidazole, nimorazole, NLA-1, NLP-1), a nitroacridine, a nitroquinoline, a nitropyrazoloacridine, olivomycin, phleomycin, a phthalanilide (e.g., propamidine or stilbamidine), pibenzimol, plicamycin, rifamycin, rhizoxin, squalamine, tanespimycin (17-allylaminogeldanamycin), or a derivative or salt of any of the foregoing.

In some embodiments, the additional agent comprises an aziridoquinone (e.g., mitomycin C, BMY-42355, AZQ or EO-9).

In some embodiments, the additional agent comprises a 2-nitroimidazole such as misonidazole, NLP-1 or NLA-1, a nitroacridine, a nitroquinoline, a nitropyrazoloacridine, a In some embodiments, the additional agent comprises an anti-inflammatory agent such as, for example, a steroid or a non-steroidal anti-inflammatory drug. Non-limiting examples of steroids include prednisone, prednisolone, methylprednisolone, dexamethasone, budenoside, fluocortolone or triamcinolone. Non-limiting examples of additional anti-inflammatory agents include acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, flufprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam, nimesulide, meloxicam, celecoxib, and rofecoxib.

In some embodiments, the additional agent comprises a biphosphonate or derivative thereof, such as, for example, minodronic acid or its derivatives (YM-529, Ono-5920, YH-529), zoledronic acid monohydrate, ibandronate sodium hydrate or clodronate disodium.

In some embodiments, the additional agent is in the form of a pharmaceutically acceptable salt, hydrate and/or solvate. In some embodiments, the chemotherapeutic agent is in the form of an individual optical isomer, a mixture of individual enantiomers, or a racemate thereof.

E. Nucleic Acids

In some embodiments, the composition comprises a nucleic acid (e.g., a DNA or RNA molecule) encoding s polypeptide antigen described herein, such an α-lactalbumin polypeptide. In such embodiments, the composition can comprise the nucleic acid instead of or in addition to an antigen. In some embodiments the composition comprises an expression vector comprising an open reading frame encoding a polypeptide, e.g., an α-lactalbumin polypeptide.

When taken up by a cell (e.g., muscle cell, an antigen-presenting cell (APC) such as a dendritic cell, macrophage, etc.), a DNA molecule can be present in the cell as an extrachromosomal molecule and/or can integrate into the chromosome. DNA can be introduced into cells in the form of a plasmid which can remain as separate genetic material. Alternatively, linear DNAs that can integrate into the chromosome can be introduced into the cell. Optionally, when introducing DNA into a cell, reagents which promote DNA integration into chromosomes can be added.

II. Therapeutic Methods

In one aspect, provided are methods comprising administering to a subject a therapeutically effective amount of a composition as disclosed herein.

In some embodiments, provided herein are methods for treating or preventing cancer and/or for inducing an immune response against a cancer, e.g., breast cancer.

Subjects

The methods described herein can be used to treat any subject in need thereof.

Generally, subjects to which presently disclosed compositions or formulations are administered have an adaptive immune system. In some embodiments, subjects are mammals. Examples of subjects include, without limitation, humans, livestock, dogs, cats, mice, rats, and transgenic species thereof. In some embodiments, subjects are humans.

In some embodiments, the subject has cancer or is at risk of developing cancer. For example, the subject may have been diagnosed with cancer. The cancer may be a primary cancer or a metastatic cancer. Subjects may have any stage of cancer, e.g., stage I, stage II, stage III, or stage IV with or without lymph node involvement and with or without metastases. Provided compositions may prevent or reduce further growth of the cancer and/or otherwise ameliorate the cancer (e.g., prevent or reduce metastases).

In some embodiments, the subject does not have cancer but has been determined to be at risk of developing cancer, e.g., because of the presence of one or more risk factors such as environmental exposure, presence of one or more genetic mutations or variants, family history, etc.

In some embodiments, the subject has not been diagnosed with cancer. For example, provided compositions and formulations may be used as a preventative vaccine, e.g., in individuals identified as a being at risk, in one or more subpopulations in which prevention may be particularly effective, etc. For example, in the context of vaccines against breast cancer, the subject may be, e.g., a non-lactating female.

In some embodiments, the cancer is breast cancer (e.g., a primary breast cancer, a metastatic breast cancer). In some embodiments, the breast cancer is a triple-negative breast cancer (negative for estrogen receptor (ER), progesterone receptor (PR), and HER2) or comprises cells that are triple-negative. In some embodiments the breast cancer is positive for or comprises cells that are positive for at least one of ER, PR, and HER2.

In some embodiments, the subject has undergone surgery to remove at least part of a breast tumor. In some embodiments, the subject is genetically predisposed to developing breast cancer due to having mutations associated with such risk, e.g., mutations in the BRCA1 or BRCA2 gene. In some embodiments, the subject has a family history of breast cancer.

In some embodiments, the cancer expresses or overexpresses a polypeptide that is used as an antigen, or a polypeptide whose fragment(s) and/or variants(s) are used as an antigen, in a provided composition or formulation. For example, in some embodiments, the cancer (e.g., a breast cancer) expresses or overexpresses α-lactalbumin.

In some embodiments, the subject has been administered, will be administered, or is simultaneously administered an additional therapy. The additional therapy may comprise, e.g., surgical resection, radiotherapy, chemotherapy, and/or other modes of immunotherapy. In some embodiments, the additional therapy comprises an additional agent as described herein.

For example, in some embodiments, the subject has been administered, will be administered, or is simultaneously administered an anti-cancer therapy comprising an anti-cancer agent as described herein.

In some embodiments, administration is timed relative to the additional therapy in a manner so as to avoid interfering with the immunogenicity of a composition as described herein.

In some embodiments, the subject has been administered an additional therapy, and, as a result of the additional therapy, the subject presents no clinical symptoms of the disease for which the subject is being treated, e.g., no clinically measurable tumor. However, in some embodiments, the subject is determined to be at risk for recurrence or progression of the disease. For example, when the disease is cancer, the subject may, in some embodiments, be determined to be at risk for recurrence or progression of cancer, e.g., near the original tumor site and/or at metastatic sites. Such subjects can be further categorized as high-risk and low-risk subjects. Categorization can be made on the basis of, e.g., features observed before and/or after treatment with the additional therapy. These features are known in the clinical arts and may be defined for each type of cancer. Features typical of high-risk subgroups include invasion of neighboring tissues, and/or involvement of lymph nodes. Thus, for example, a pharmaceutical composition described herein can be administered to the subject to elicit an anti-cancer response to prevent recurrence or progression of cancer.

Routes of Administration

Compositions (including pharmaceutical compositions) disclosed herein may be administered by any suitable route of administration, including orally, parenterally, and other routes of administration discussed in the "Formulations and Pharmaceutical Compositions" subsection of the "Compositions" section. In some embodiments, a therapeutically effective amount of the composition is administered by a systemic route of administration (e.g., via oral or parenteral administration). In some embodiments, a therapeutically effective amount of the composition is administered locally. In some embodiments, a therapeutically effective amount of the composition is administered by subcutaneous, intradermal, subdermal, or intramuscular injection.

Dosages

In certain embodiments, the therapeutically effective amount comprises more than one dose, e.g., at least two doses or at least three doses. In some embodiments, the therapeutically effective amount comprises no more than three doses, e.g., exactly three doses. In some embodiments, each dose is administered one or more weeks apart, e.g., at least two or more weeks apart, at least three or more weeks apart, or at least four weeks apart. In some embodiments, each dose is administered about four weeks apart.

In some embodiments, each dose contains approximately the same amount of antigen. In some embodiments, each dose contains approximately the same amount of antigen and the same amount of carbohydrate.

In some embodiments, an initial dose is administered, and the subject is monitored for an immunological and/or clinical response. Suitable means of immunological monitoring include using patient's peripheral blood mononuclear cells (PBMC) as responders and neoplastic cells or the antigen as stimulators for determining memory or recall responses. An immunological reaction also can be determined by presence of a delayed inflammatory response at the site of administration. One or more doses subsequent to the initial dose can be given as appropriate, for example, on a monthly, semi-monthly, or weekly basis, until the desired effect is achieved. Thereafter, additional booster or maintenance doses can be given as required, particularly when immunological or clinical benefits appear to subside.

An appropriate dosage may be determined, e.g., by reference to resulting plasma concentrations in subjects who are administered the dose. For example, the maximum plasma concentration (Cmax) and the area under the plasma concentration-time curve from time 0 to infinity (AUC (0-4)) may be used. Dosages include those that produce certain desired values for Cmax and AUC (0-4).

Dosages may depend upon a variety of factors such as, for example, activity of the particular antigen or composition;

route of administration; time of administration; rate of excretion or metabolism of components in a particular composition being employed; duration of treatment; other drugs, compounds and/or materials used in combination with the particular antigen composition; the age, sex, weight, condition, general health and prior medical history of the subject; and like factors well known in the medical arts.

In general, a "therapeutically effective amount" of a composition described herein will be that amount which is the lowest amount effective to produce a desired immunologic, prophylactic, or therapeutic effect. For example, in some embodiments, a therapeutically effective amount is an amount that is able to induce an effective humoral or cellular T cell response in the subject to be treated, or in some embodiments, an effective systemic immune response. Such an effective amount will generally depend upon certain factors such as those described above.

In some embodiments, each dose contains between about 1 µg to about 20 mg, e.g., between about 1 µg to about 5 mg, between about 50 µg to about 2 mg of antigen, or between about 100 µg to about 1 mg of antigen. For example, in some embodiments, each dose contains about 1 µg, about 2 µg, about 3 µg, about 4 µg, about 5 µg, about 10 µg, about 15 µg, about 20 µg, about 30 µg, about 40 µg, about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, or any value in between of antigen.

In some embodiments, each dose contains between about 1 µg to about 20 mg, e.g., between about 10 µg to about 10 mg, from about 50 µg to about 5 mg, from about 100 µg to about 2 mg, or from about 100 µg to about 1 mg of carbohydrate. For example, in some embodiments, each dose contains about 1 µg, about 2 µg, about 3 µg, about 4 µg, about 5 µg, about 10 µg, about 15 µg, about 20 µg, about 30 µg, about 40 µg, about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg or about 20 mg or any value in between of carbohydrate.

Responses

In some embodiments, administering the composition induces an immune response.

Generally, the immune response can include a humoral immune response, a cell-mediated immune response, or both.

A humoral response can be determined, for example, by a standard immunoassay for antibody levels in a serum sample from the subject receiving the pharmaceutical composition.

A cellular immune response is a response that typically involves T cells and can be determined in vitro or in vivo.

For example, a general cellular immune response can be determined as the T cell proliferative activity in cells (e.g., peripheral blood leukocytes (PBLs)) sampled from the subject at a suitable time following the administering of a pharmaceutically acceptable composition. For example, after incubation of PBMCs with a stimulator for an appropriate period, [$^3$H]thymidine incorporation can be determined. The percentage of proliferating T cells can be determined using flow cytometry. Another way to measure cellular immunity involves measuring circulating frequencies of T cells secreting proinflammatory Type-1 and/or Type-17 cytokines in response to the antigen.

In some embodiments, the immune response comprises an antigen-specific T cell immune response, which can comprise, for example, CD4+ T cells, CD8+ T cells, or both. In some embodiments, the T cell immune response comprises a type-1 or a type-17 proinflammatory T cell response. In some embodiments, the T cell immune response comprises both a type-1 and a type-17 proinflammatory T cell response.

When the antigen is expressed on a cell, administering the composition may elicit an immune response to that cell. For example, when the antigen is a tumor associated antigen, administering the composition may elicit an immune response to tumor cells that express the antigen.

In some embodiments, administering causes reduced granuloma formation in the subject relative to a reference level. For example, the reference level may be the level of granuloma formation observed in a subject administered a composition comprising Complete Freund's Adjuvant. In some embodiments, the reference level is the level of granuloma formation observed in a subject administered a composition comprising Incomplete Freund's Adjuvant. "Reduced granuloma formation" may be characterized, for example, by one or more of: fewer granulomas formed, granulomas of reduced severity, granulomas whose severity decreases more rapidly, and granulomas that resolve (partially or completely) more quickly.

Cell Therapy

In some embodiments, provided are methods comprising administering to a subject cells (e.g., antigen-presenting cells or precursors thereof) that have been contacted in vitro with a composition as disclosed herein, or cells that have been generated from such cells, such as antigen-primed antigen-presenting cells or antigen-specific lymphocytes.

IV. Methods of Making

In one aspect, provided are methods of making compositions or formulations as disclosed herein. Generally, such methods comprise a step of mixing an aqueous solution comprising an antigen with an emulsion comprising a carbohydrate and a metabolizable oil. Suitable antigens, carbohydrates, and metabolizable oils, as well as suitable ratios between two or more components, include those described herein, e.g., in the "Compositions" section.

For example, in some embodiments, the ratio of the aqueous solution to the emulsion is between about 1:2 to about 2:1 (v/v). In some embodiments, the ratio of the aqueous solution to the emulsion is about 1:1 (v/v).

V. Uses

In one aspect, provided are methods of using compositions or formulations as disclosed herein for the manufacture of a medicament for preventing, treating, or ameliorating a disease or condition, e.g., cancer.

This invention is further illustrated by the following examples, which should not be construed as limiting. The contents of all references, patents and published patent applications cited throughout this application, as well as the Figures, are incorporated herein by reference.

EXEMPLIFICATION

Example 1: A Single Vaccination with α-Lactalbumin in Complete Freund's Adjuvant (CFA) Induced Both Type-1 and Type-17 Proinflammatory T Cell Immune Responses Previously published studies showed that vaccination of mice with recombinant mouse α-lactalbumin inhibits growth of both autochthonous and transplantable breast tumors when used in either prophylactic or therapeutic protocols. In those experiments in which tumor growth inhibition was observed, CFA was used as an adjuvant.

In the present Example, the types of immune responses elicited by α-lactalbumin in CFA were characterized by examining splenocyte frequencies of type-1 (IFNγ-producing) and type-17 (IL-17-producing) T cells in mice administered α-lactalbumin/CFA compositions.

Mice were administered a single subcutaneous injection of 100 μg of recombinant mouse α-lactalbumin in CFA (containing 200 μg H37Ra *Mycobacterium tuberculosis*). As shown in FIG. 1, mean splenocyte frequencies of α-lactalbumin-specific T cells producing IFNγ (type-1) and IL-17 (type-17) proinflammatory T cells respectively reached levels of $\frac{1}{6,700}$ and $\frac{1}{12,700}$ (FIG. 1).

Therefore, a single injection of an α-lactalbumin/CFA composition was sufficient to elicit a proinflammatory immune response comprising both type-1 and type-17 T cells.

Example 2: Development of an Alternative Adjuvant that Elicits Both Type-1 and Type-17 T Cell Responses As Example 1 demonstrates, an antigen/CFA composition elicits both type-1 and type-17 T cell responses, suggesting that CFA is an effective immune-stimulating adjuvant.

Figure 2:
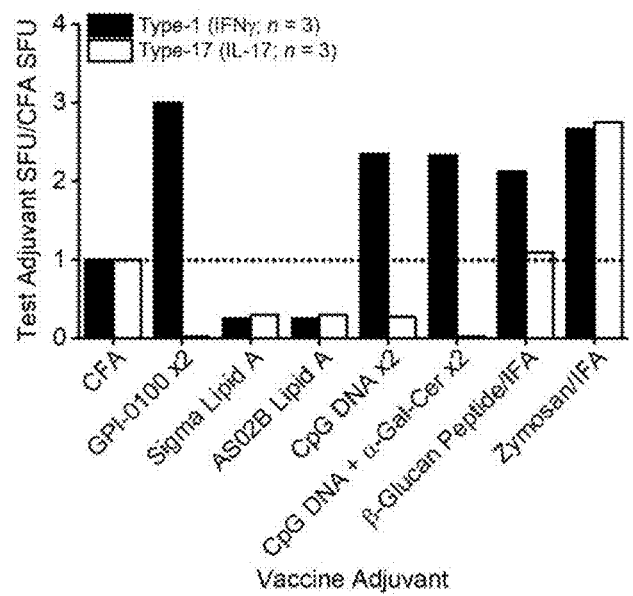
FIG. 2 shows the comparison of several adjuvants with CFA in inducing type-1/type-17 T cell immunity. Splenocyte frequencies of type-1 and type-17 proinflammatory T cells were measured 4 weeks after immunization of 6-8-week-old BALB/cJ female mice with 200 μL of an emulsion containing 100 μg recombinant mouse α-lactalbumin and conventional doses of various adjuvants including CFA. Data are expressed as mean α-lactalbumin-specific type-1 and type-17 spot forming units (SFU) obtained using each test adjuvant divided by the SFU obtained on the same day using CFA as the "gold standard" adjuvant. The horizontal black-dotted line indicates frequencies equivalent to those obtained using CFA as adjuvant (SFU elicited using CFA=1). Some immunizations were performed twice, two weeks apart and are indicated by ×2.

Unfortunately, CFA cannot be used as an adjuvant in human vaccination because of its toxic effects, which are primarily related to its induction of unresolved granulomas and abscesses at the site of vaccination. To develop an alternative, non-toxic adjuvant that mimics CFA by inducing similar high frequencies of α-lactalbumin-specific type-1 and type-17 T cells, a series of adjuvants were tested with the goal of "reverse engineering" the optimized type-1/type-17 adaptive immune response induced by CFA. The tested adjuvants included: 1) CFA at 200 μg/vaccination, 2) GPI-0100, a triterpene glycoside, used at 200 μg/vaccination, 3) Sigma Lipid A (Ribi adjuvant) used at 50 μg/vaccination, 4) ASO2B Lipid A at 50 μg/vaccination, 5) non-methylated CpG DNA used at 100 μg/vaccination, 6) α-Galactosyl-Ceramide (α-Gal-Cer) at 10 μg/vaccination, 7) β-Glucan Peptide at 200 μg/vaccination in IFA, and 8) zymosan at 200 μg/vaccination in IFA. Each vaccine dose contained 100 μg of recombinant mouse α-lactalbumin protein in 100 μL aqueous solution emulsified with 100 μL of adjuvant prepared according to manufacturers' recommendations, if available. In the absence of such recommendations, adjuvants were prepared according to instructions provided in literature references demonstrating induction of substantial immune responses. Of the adjuvants tested with recombinant mouse α-lactalbumin, β-Glucan Peptide/IFA and zymosan/IFA were the only adjuvants that induced frequencies of type-1 and type-17 T cells that are associated with tumor immunity and that are similar to those observed using CFA as adjuvant (FIG. 2).

Figure 3A:
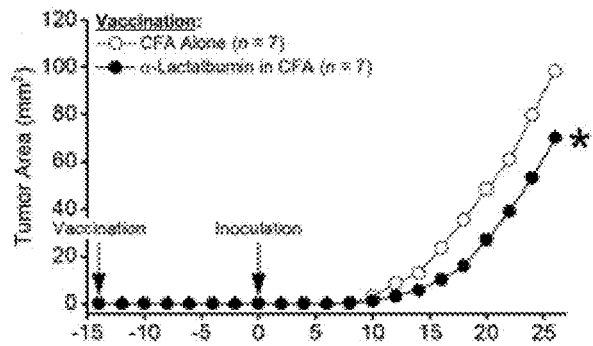
FIG. 3A-FIG. 3H show 4T1 mouse breast tumor growth using different α-lactalbumin/adjuvant combinations.
Figure 3B:
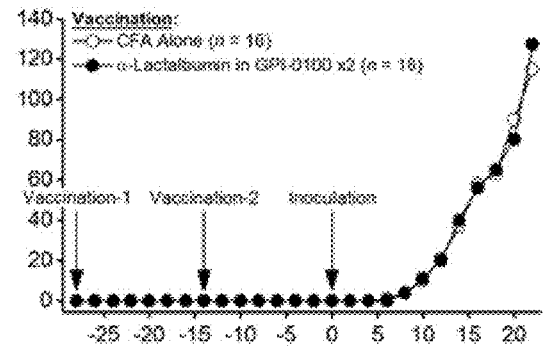
Figure 3C:
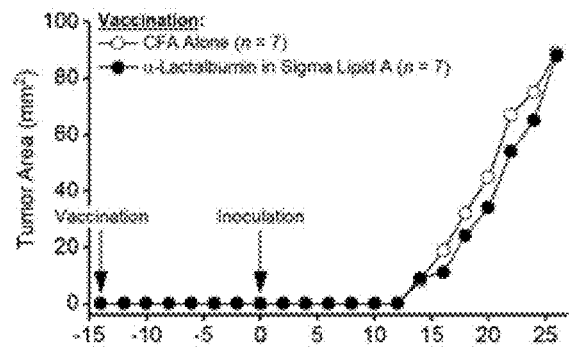
Figure 3D:
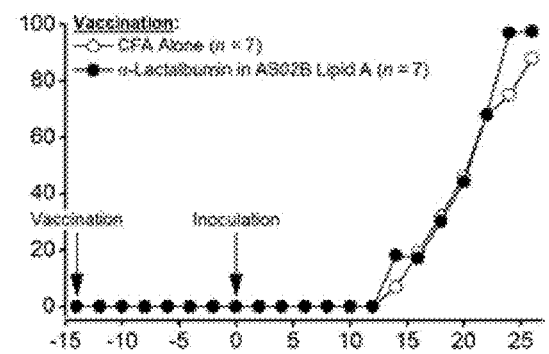
Figure 3E:
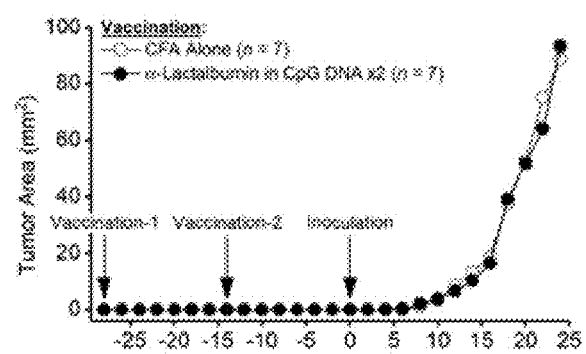
Figure 3F:
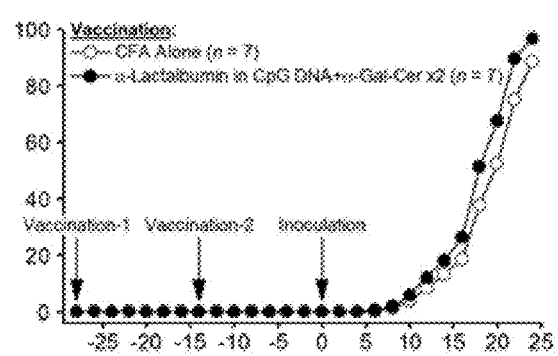
Figure 3G:
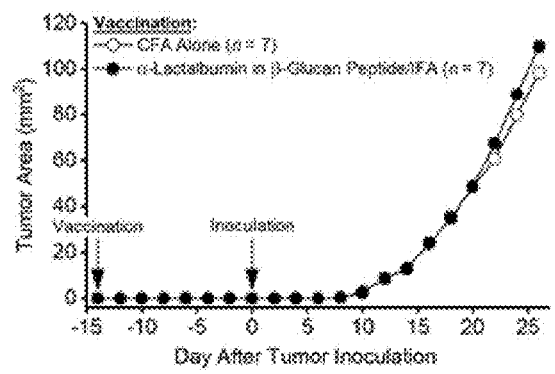
Figure 3H:
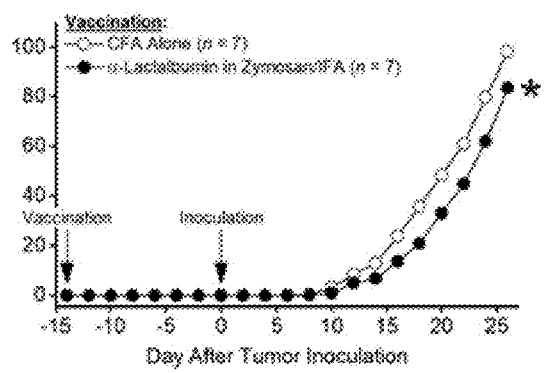

In subsequent preclinical testing for inhibition of breast tumor growth in vivo, the only immunogen/adjuvant combination that provided significant inhibition of 4T1 mouse breast tumor growth comparable to that observed using α-lactalbumin/CFA (FIG. 3A; P<0.02) was α-lactalbumin using zymosan in IFA as adjuvant (FIG. 3H; P<0.02). All other tested adjuvants failed to provide any in vivo inhibition of breast tumor growth (FIG. 3B-G).

These results suggest that zymosan combined with IFA is an effective adjuvant in vaccine compositions. Moreover, an anti-cancer vaccine comprising zymosan, IFA, and an antigen expressed on cancer cells successfully inhibited growth of tumors in vivo.

Example 3: Development of a Non-Toxic Adjuvant that Elicits Both Type-1 and Type-17 Responses A substantial part of the toxic effects induced by CFA may very well be due to the IFA used to suspend the dead Mycobacteria tuberculosis. IFA is often used as a stand-alone adjuvant for inducing type-2 regulatory T cells and production of antibodies. IFA is prepared from non-metabolizable oils including paraffin oil. These non-metabolizable oils linger and facilitate antigen presentation over an extended time period. However, this lingering may contribute substantially to the unresolved granulomas and abscesses at sites of vaccination observed with CFA. Thus, to develop a non-toxic alternative adjuvant acceptable for use in human vaccination that, together with an antigen, elicits high frequencies of antigen-specific type-1 and type-17 proinflammatory T cells, a substitute for IFA was sought. This substitute could then be used together with zymosan as a vaccine adjuvant.

MONTANIDE™ ISA 51 VG (Seppic, Paris, France) was tested as a potential substitute for IFA. MONTANIDE™ ISA 51 VG is a GMP-grade mixture of a highly purified mineral oil (DRAKEOL™ 6 VR) and a surfactant (Mannide monooleate). When mixed with an aqueous phase immunogen in a 50/50 ratio, it renders a water-in-oil emulsion. Like IFA, this water-in-oil emulsion acts as a stand-alone vaccine for producing enhanced immune responses. MONTANIDE™ ISA 51 VG serves as a replacement for MONTANIDE™ ISA 51. The difference between both grades is the origin of the oleic acid used to manufacture the surfactant (Mannide Monooleate). The oleic acid used to make MONTANIDE™ ISA 51 is of animal origin. Because of concerns about bovine spongiform encephalopathy (BSE) and other transmissible spongiform encephalopathies, the oleic acid used in MONTANIDE™ ISA 51 VG is of vegetable origin. Since 2006, MONTANIDE™ ISA 51 VG (hereinafter in this Example referred to simply as "MONTANIDE™") has been used in over 150 human clinical trials worldwide involving over 10,000 patients. Detailed composition, manufacturing process, analytical controls, and stability data are described in the Drug Master Files (DMF) or the Common Technical Document (CTD) registered in different countries (DMF type IV No 9756 and No 10870 in the USA; BBMF No 12130 and 14167 in the USA).

To test MONTANIDE™'s suitability as an adjuvant ingredient, female BALB/cJ mice at 6-8 weeks of age were administered a single dose of an emulsion containing 100 μg of recombinant mouse α-lactalbumin and 200 μg of zymosan in either 100 µL of IFA or 100 µL of MONTANIDE™. Four weeks after vaccination, splenocyte frequencies of proinflammatory type-1 (IFNγ) and type-17 (IL-17) T cells were determined by ELISPOT analysis. The data in FIG. 4 show mean spot forming units (SFU) in recall responses to 50 µg/mL of recombinant mouse α-lactalbumin minus mean background responses of cultures containing no recall antigen (mean background <5 SPU per assay).

Figure 4:
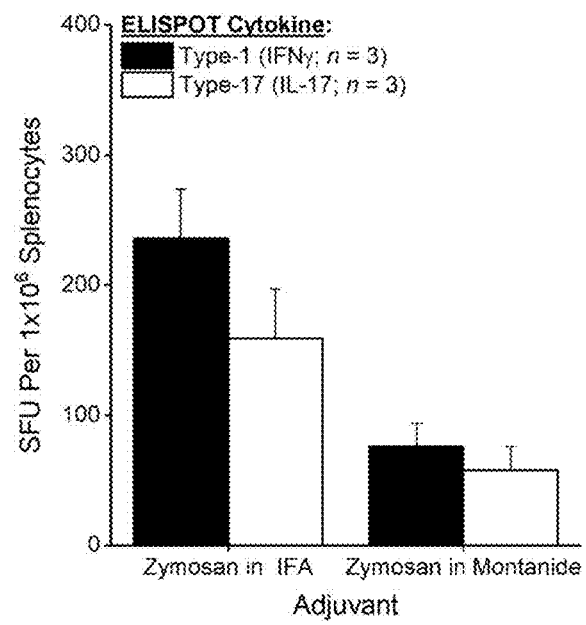
FIG. 4 shows induction of type-1/type-17 proinflammatory T Cells Using Zymosan/IFA vs. Zymosan/MONTANIDE™. Female BALB/cJ mice at 6-8 weeks of age were vaccinated with an emulsion containing 100 μg of aqueous phase recombinant mouse α-lactalbumin emulsified with 200 μg of zymosan in either 100 μL of IFA or 100 μL of MONTANIDE™. Four weeks after vaccination, splenocyte frequencies of proinflammatory Type-1 (IFNγ) and Type-17 (IL-17) T cells were determined by ELISPOT analysis. Data show mean spot forming units (SFU) in recall responses to 50 μg/mL of recombinant mouse α-lactalbumin minus mean background responses of cultures containing no recall antigen (mean background <5 SPU per assay). Error bars indicate ±SE.

As shown in FIG. 4, when zymosan and MONTANIDE™ were used as an adjuvant, production of both type-1 and type-17 proinflammatory T cells were induced. However, the level of induction was much lower than that achieved using zymosan in IFA as adjuvant. Thus, multiple doses of vaccine comprising zymosan/MONTANIDE™ as an adjuvant may be required to achieve the high T cell frequencies associated with inhibition of tumor growth.

These results indicate that an adjuvant comprising zymosan in a metabolizable oil can support an antigen in eliciting both type-1 and type-17 immune responses.

Example 4: Effective Doses of an α-Lactalbumin/Zymosan/MONTANIDE™ Vaccine

To determine the effective dose or doses needed to provide high frequencies of α-lactalbumin-specific Type-1/Type-17 T cells using the zymosan/MONTANIDE™ adjuvant combination, female BALB/c mice were administered one or more doses of a 200 µL emulsion containing equal amounts (by weight) of α-lactalbumin and zymosan. Each dose contained between 100-1000 µg each of α-lactalbumin and zymosan.

Recombinant mouse α-lactalbumin (FLAG-N-mαlac-C-HIS) was solubilized in sterile USP grade water, and zymosan was suspended in MONTANIDE™ ISA 51 VG. Four weeks after the final vaccination, splenocytes underwent ELISPOT analysis using capture/antibody pairs specific for mouse IFNγ, IL-5, and IL-17 to assess generated splenocyte frequencies of type-1, type-2, and type-17 T cell lineages, respectively.

Each group of three mice received one, two, or three doses spaced four weeks apart. Four weeks after the final dose, splenocyte frequencies of type-1 proinflammatory T-cells, type-17 proinflammatory T cells, and type-2 regulatory T cells were determined by ELISPOT analysis using capture/antibody pairs specific for mouse IFNγ, IL-17, and IL-5 respectively.

Figure 5:
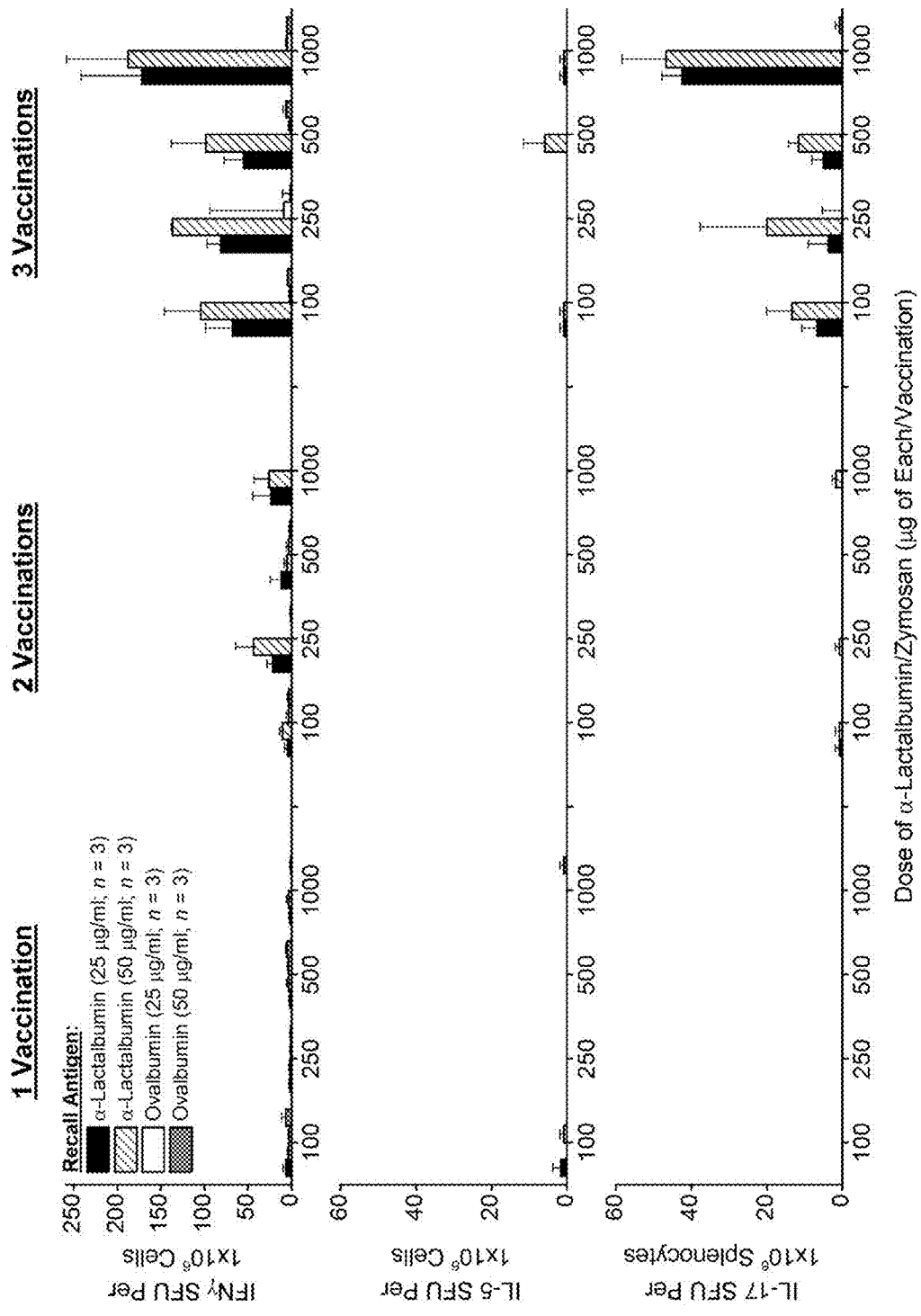
FIG. 5 shows results from vaccine dosage studies. Eight-week old female BALB/cJ mice were vaccinated subcutaneously in the abdominal flank with 200 μl of emulsion containing equal amounts of α-lactalbumin and zymosan ranging from 100-1000 μg each. Recombinant mouse α-lactalbumin (FLAG-N-mαlac-C-HIS) was solubilized in sterile USP grade water, and zymosan was suspended in MONTANIDE™ ISA 51 VG. Groups of 3 mice each received either one, two, or three vaccinations spaced four weeks apart. Four weeks after the final vaccination, splenocytes underwent ELISPOT analysis using capture/antibody pairs specific for mouse IFNγ, IL-5, and IL-17 to assess generated splenocyte frequencies of Type-1, Type-2, and Type-17 T cell lineages, respectively.

As shown in FIG. 5, at all doses tested (100 µg, 250 µg, 500 µg, and 1000 µg each of α-lactalbumin and zymosan), both type-1 and type-17 responses were elicited after the third dose. Consistent production of high frequencies of type-1/type-17 T cells occurred after three doses with emulsions containing 1 mg α-lactalbumin/1 mg zymosan (FIG. 5).

Additionally, no abscesses were observed at any dose, and all granulomas produced at the site of vaccination were completely resolved within 1-2 weeks following vaccination. No long-term adverse effects were observed. Accordingly, α-lactalbumin/zymosan/MONTANIDE™ is an effective immunogen/adjuvant combination for inducing α-lactalbumin-specific type-1 and type-17 T cells at frequencies typically sufficient to inhibit breast tumor growth without inducing unresolved granulomas and abscesses at the vaccination site.

In summary, results described in Examples 2-3 indicate that vaccination with α-lactalbumin/zymosan/IFA induces a type-1/type-17 T cell immunity and inhibition of breast tumor growth similar to vaccination with α-lactalbumin/CFA. When zymosan is suspended in MONTANIDE™ instead of IFA, the resulting water-in-oil emulsions, when used with a suitable antigen, induce antigen-specific type-1/type-17 proinflammatory T cells, though at lower frequencies than observed with IFA. In addition, multiple high dose vaccinations with emulsions of α-lactalbumin/zymosan/MONTANIDE™ induce type-1/type-17 T cell frequencies associated with inhibition of breast tumor growth without inducing abscesses or unresolved granulomas. Thus, vaccination with α-lactalbumin/zymosan/MONTANIDE™ emulsions induces the type-1/type-17 immunity associated with effective inhibition of breast tumor growth.

Example 5: Toxicology Profile of α-Lactalbumin/Zymosan/MONTANIDE™ Vaccines

To evaluate whether an adjuvant comprising zymosan in MONTANIDE™ was associated with toxic effects, histopathology and biometrics of mice vaccinated with recombinant α-lactalbumin/zymosan/MONTANIDE™ were examined.

Study Design

Three groups of 25 mice each (groups A, B, and C) respectively received 1, 2, or 3 doses. Each group was subdivided into 5 subgroups of 5 mice each, with each subgroup receiving: 1) a control vaccine; 2) a vaccine with 100 µg recombinant mouse α-lactalbumin (FLAG-N-mαlac-C-HIS variant); 3) a vaccine with 1000 µg recombinant mouse α-lactalbumin (FLAG-N-mαlac-C-HIS variant); 4) a vaccine with 100 µg recombinant human α-lactalbumin (HISTEV-N-hαlac-COOH variant); and 5) a vaccine with 1000 µg recombinant human α-lactalbumin (HISTEV-N-halac-COOH variant). All vaccines were water-in-oil emulsions having equal volumes of aqueous phase recombinant α-lactalbumin as the target antigen and oil phase zymosan as adjuvant in MONTANIDE™ ISA 51 VG.

Group A mice received a single dose, group B mice received two doses one month apart, and group C mice group received three doses one month apart, as outlined in Table 2.

TABLE 2

Study design

| Group | Subgroup ID (5 mice/subgroup) | Immunogen | Adjuvant |
|---|---|---|---|
| A One Vaccination (n = 25) | C0 | — | — |
| | M100 | 100 µg FLAG-N-mαlac-C-HIS | 100 µg zymosan |
| | M1000 | 1000 µg FLAG-N-mαlac-C-HIS | 1000 µg zymosan |
| | H100 | 100 µg HISTEV-N-hαlac-COOH | 100 µg zymosan |
| | H1000 | 1000 µg HISTEV-N-hαlac-COOH | 1000 µg zymosan |
| B Two Vaccinations (n = 25) | C0 | — | — |
| | M100 | 100 µg FLAG-N-mαlac-C-HIS | 100 µg zymosan |
| | M1000 | 1000 µg FLAG-N-mαlac-C-HIS | 1000 µg zymosan |
| | H100 | 100 µg HISTEV-N-hαlac-COOH | 100 µg zymosan |
| | H1000 | 1000 µg HISTEV-N-hαlac-COOH | 1000 µg zymosan |

TABLE 2-continued

Study design

| Group | Subgroup ID (5 mice/subgroup) | Immunogen | Adjuvant |
|---|---|---|---|
| C | C0 | — | — |
| Three Vaccinations (n = 25) | M100 | 100 µg FLAG-N-mαlac-C-HIS | 100 µg zymosan |
| | M1000 | 1000 µg FLAG-N-mαlac-C-HIS | 1000 µg zymosan |
| | H100 | 100 µg HISTEV-N-hαlac-COOH | 100 µg zymosan |
| | H1000 | 1000 µg HISTEV-N-hαlac-COOH | 1000 µg zymosan |

Materials and Methods
Recombinant α-Lactalbumin

Open reading frame cDNA nucleotide sequences for mouse α-lactalbumin (NCBI reference sequence: NM_010679.1) and human α-lactalbumin (NCBI reference sequence: NM_002289.2) were modified to ensure optimized protein folding and production in prokaryotic expression systems by substituting mammalian codons with more efficient prokaryotic sequences coding for the same amino acid (Dapcel, Cleveland, Ohio). Optimized DNA sequences were synthesized de novo (GeneArt, Regensburg, Germany). Murine α-lactalbumin DNA was inserted into the pET3a expression vector, (GeneArt) to provide a recombinant mouse α-lactalbumin containing an N-terminal FLAG-tag and a C-terminal 6×His-tag (FLAG-N-mαlac-C-HIS). Human α-lactalbumin DNA was also inserted into the pET3a expression vector (GeneArt) to provide a recombinant human α-lactalbumin containing a 6×His-tag linked to the N-terminus with the tobacco etch virus nuclear-inclusion-a endopeptidase (TEV protease) that serves as a cleavage site for removing the 6×His-tag from the recombinant human α-lactalbumin protein (HISTEV-N-hαlac-COOH). Plasmids containing these inserts were transformed in *E. coli* strain BL21 Star (Invitrogen, Carlsbad, Calif.). High-level expression colonies were selected following induction with isopropyl β-D-1-thiogalactopyranoside (IPTG; Amresco, Solon, Ohio) and were sequenced to confirm proper orientation and alignment. 6×His-tagged proteins were purified under denaturing and reducing conditions using nickel-nitrilo triacetic acid (Ni-NTA) affinity chromatography (Qiagen Sciences, Germantown, Md.). Prior to use in vitro, proteins were purified by reverse phase high performance liquid chromatography (HPLC) to obtain endotoxin-free protein.

Water

Sterile USP grade water was obtained commercially (Corning) and used to solubilize recombinant α-lactalbumin proteins in the aqueous phase of the emulsion.

Zymosan

Zymosan A was obtained commercially (Sigma-Aldrich) and used as a vaccine adjuvant.

MONTANIDE™ MONTANIDE™ ISA 51 VG was obtained commercially (Seppic) and used as a solvent to suspend zymosan and to maintain and stabilize the emulsion phase.

Vaccine Preparation

Recombinant α-lactalbumin protein solutions were adjusted to a concentration of 10 mg/ml in sterile USP grade water to make a stock solution. Zymosan was suspended in MONTANIDE™ ISA 51 VG at a concentration of 10 mg/ml to make a stock solution. To vaccinate at the high dose of 1000 µg recombinant α-lactalbumin+1000 µg zymosan, one 3.0 ml syringe was loaded with the aqueous recombinant α-lactalbumin solution and locked into a double female luer lock connector, and another syringe was loaded with an equal volume of the oil phase zymosan suspension and locked into the other end of the connector.

Emulsification comprised two stages: a pre-emulsification at a very slow speed and a final emulsification at a high speed. The syringe plunger containing aqueous recombinant α-lactalbumin was pushed completely so that both phases were in one syringe. During the slow pre-emulsion stage, the entire formulation was slowly and repeatedly passaged from one syringe to the other syringe through the connector for a total of 30 cycles that took 4 seconds for each plunge (each cycle taking 8 seconds to complete). At the end of this pre-emulsion stage, the speed was dramatically increased so that 80 additional complete cycles were made as quickly as possible. The entire emulsion was then plunged into one syringe and a sterile 26 gauge needle was connected.

Creation of a stable emulsion was confirmed prior to vaccination by the drop test: the emulsion was deemed stable if a drop of the emulsion maintained its structural integrity for at least 5 minutes when placed in a beaker filled with water. 200 µl of the emulsion was injected subcutaneously into the dorsal neck region to provide a high dose vaccine (1000 µg recombinant α-lactalbumin+1000 µg zymosan). To create an emulsion containing a low dose vaccine (100 µg recombinant α-lactalbumin+100 µg zymosan), stock reagents were diluted to 10% of their original concentration with appropriate solvent before emulsion preparation.

Mice and Vaccine Administration

Female BALB/cJ mice were obtained commercially (Jackson Laboratory, Bar Harbor, Me.) at 6-7 weeks of age and vaccinated at 8-10 weeks of age.

Mice were subcutaneously injected in the dorsal neck area with 200 µl of emulsion for each dose. All vaccinations were performed on the dorsal side, beginning near the back of the scalp, and continuing in subsequent vaccinations in the caudal direction about 1.5 cm away from each prior vaccination.

To facilitate precision injections, mice were immobilized under isoflurane anesthesia before being administered each dose. After receiving each dose, mice were housed and maintained in microisolator cages, with free access at all times to sterilized food and water. Mice were observed daily for any changes in behavior including altered social activity, isolation, altered appearance or grooming behavior, excessive attention to the injection site, excessive scratching, etc.

Biometrics

Baseline weights and body temperatures were obtained immediately before each dose and every three days thereafter. Changes in body weight and body temperature over the course of the experiments were plotted as a percent of deviation from baseline, with the day 0 weight serving as 100%. Body temperatures were obtained using an Optris LS IR thermometer (Micro-Epsilon, Raleigh, N.C.), with the temperature probe placed at the same distance from the xiphoid process for each measurement. Weights of livers, spleens, and kidneys were determined at necropsy and calculated as percentage of total body weight for each mouse.

Necropsy

Mice from each group were housed in a single cage with each mouse individually distinguished by distinct permanent ear punches and secondarily by temporary tail markers. Mice were euthanized 14-16 days after their final vaccination.

On the day of necropsy, one cage at a time was placed under a chemical fume hood where necropsies were performed. Mice were observed for grooming patterns and condition of injection sites.

Body temperatures and body weights were recorded, and the mice were then placed in a chamber connected to an isoflurane vaporizer that supplies 97.5% pure oxygen and 2.5% isoflurane. After deep anesthesia, mice were placed ventral side up and swabbed on the thoracic region with 70% isopropyl alcohol prep pads for cardiac puncture with a 1.0 ml syringe and a 22 gauge needle. After collecting approximately 0.5-0.8 ml whole blood, mice were cervically dislocated, and a midline ventral incision was made in the abdominal wall with a surgical scissors from the lower abdomen to the xiphoid process, exposing the abdominal contents. An incision was then made through the diaphragm, cutting through the thoracic cage. The vena cava was cut to allow a perfusion exit and a 26 gauge needle on a 30 ml syringe filled with cold sterile PBS was inserted into the left ventricle for perfusion. The mouse was slowly perfused with a total volume of 30 ml cold PBS. The spleen, liver, and kidneys were removed and weighed before being placed in 10% phosphate-buffered formalin. Thereafter, remaining tissues to be collected were carefully removed and placed in fixative. Twenty-four hours later, tissues were removed, washed with PBS, and placed in 70% ethanol until processing for histopathology. Brains from group C mice were fixed for an extended period of time before being stored in 70% ethanol.

Histopathology

These tissues were collected for histopathology: kidney, brain, large intestine, liver, lung, ovary, spleen, heart, uterus, skin (injection site), stomach, bladder, breast, and small intestine. Starting with groups B and C, skin samples from each injection site were collected to allow evaluation of the healing process of injection sites over time. For group C, additional tissues including thymus, mesenteric lymph nodes, and mandibular salivary glands were collected and analyzed. Tissue processing was also modified for group C to include 1) inflation of the bladder and lungs with formalin as part of the collection process; and 2) formalin fixation of the brain in the cranium with the calvaria removed for a total of five days instead of 24 hours of fixation. All tissues were fixed in 10% phosphate-buffered formalin overnight, washed with PBS, and stored in 70% ethanol until processing. Tissues were paraffin-embedded, cut, mounted on slides, and stained with hematoxylin and eosin. Tissue sections were analyzed by a veterinary pathologist.

Results

Figure 6:
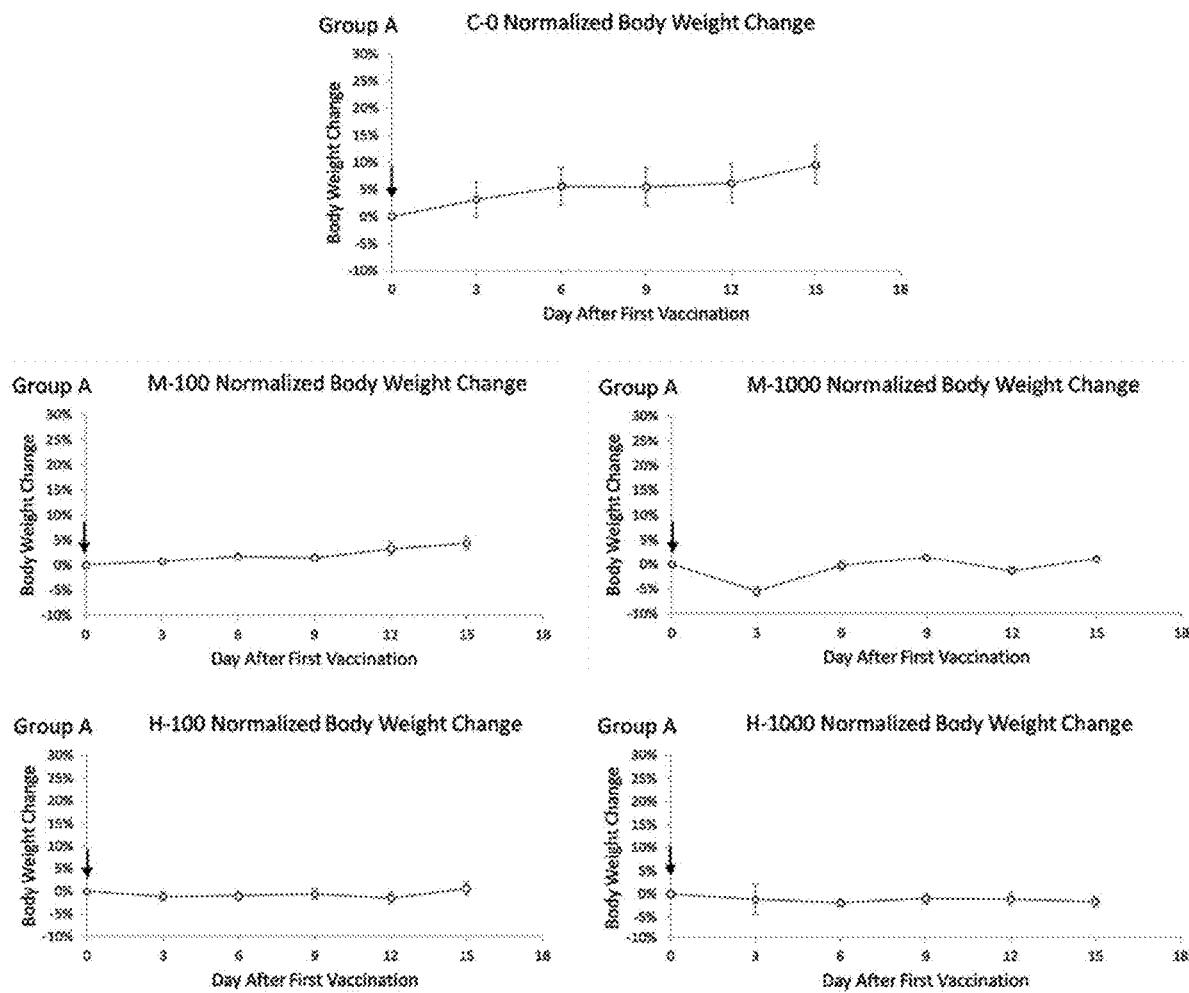
FIGS. 6-8 show changes in body weights from the time of first vaccination for the single vaccination group A mice (FIG. 6), the double vaccination group B mice (FIG. 7), and the triple vaccination group C mice (FIG. 8) in the toxicology study described in Example 5. Body weight changes were normalized to the weight obtained on day 0 (set as 100%) and plotted as a percentage increase or decrease relative to this initial starting point. Weights were recorded at the same time of day for each mouse. Arrows indicate day(s) of vaccination. Error bars indicate ±SE.
Figure 7:
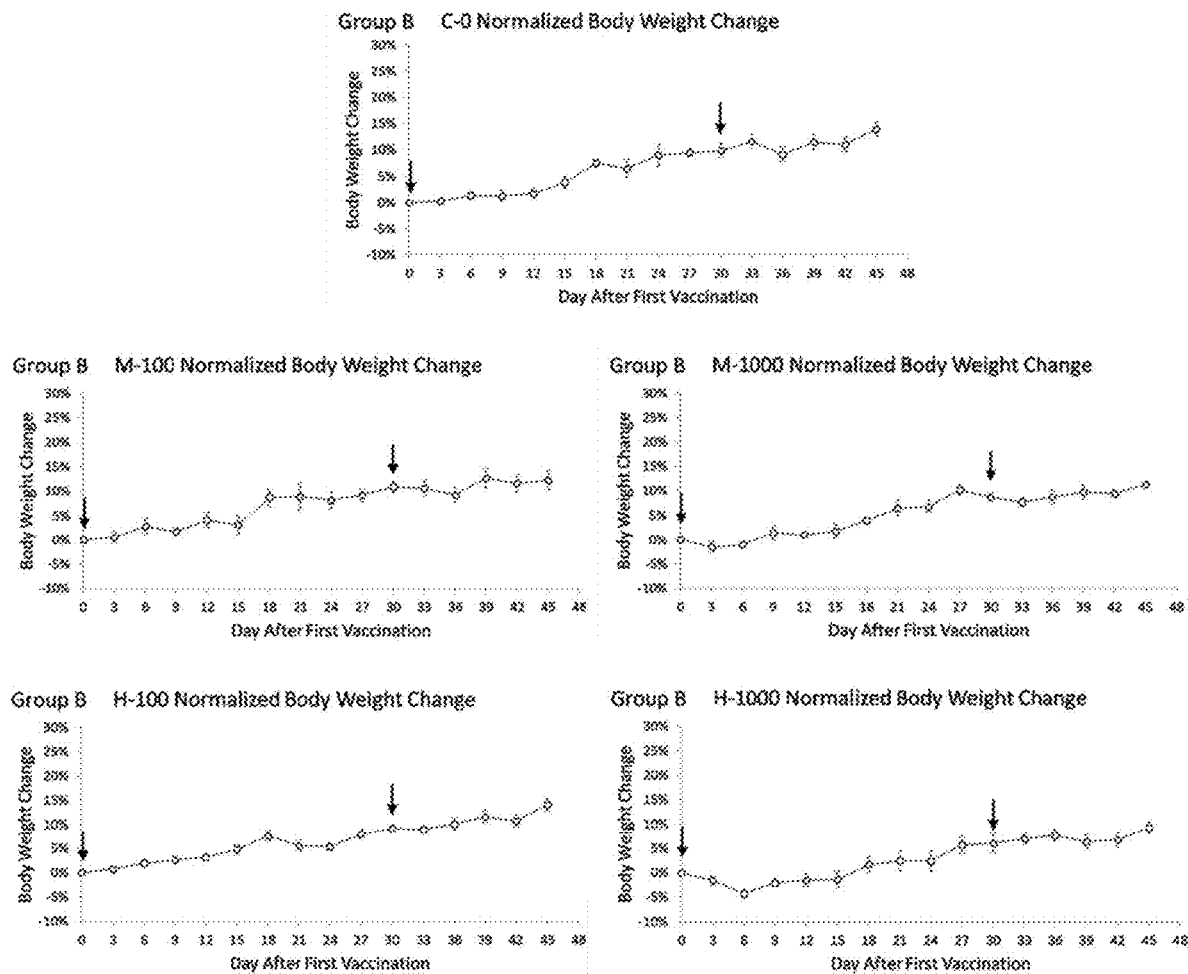
Figure 8:
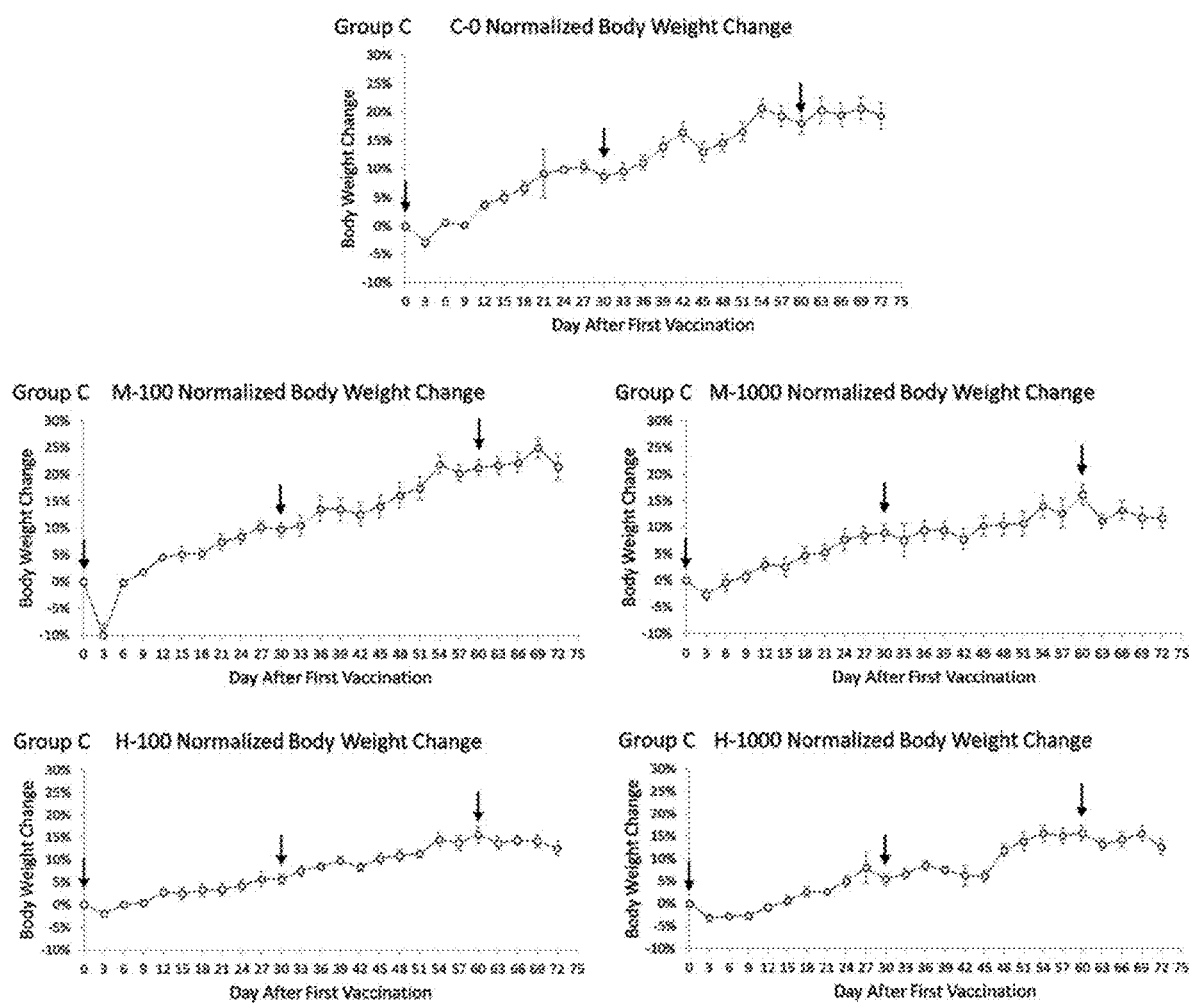
Figure 9:
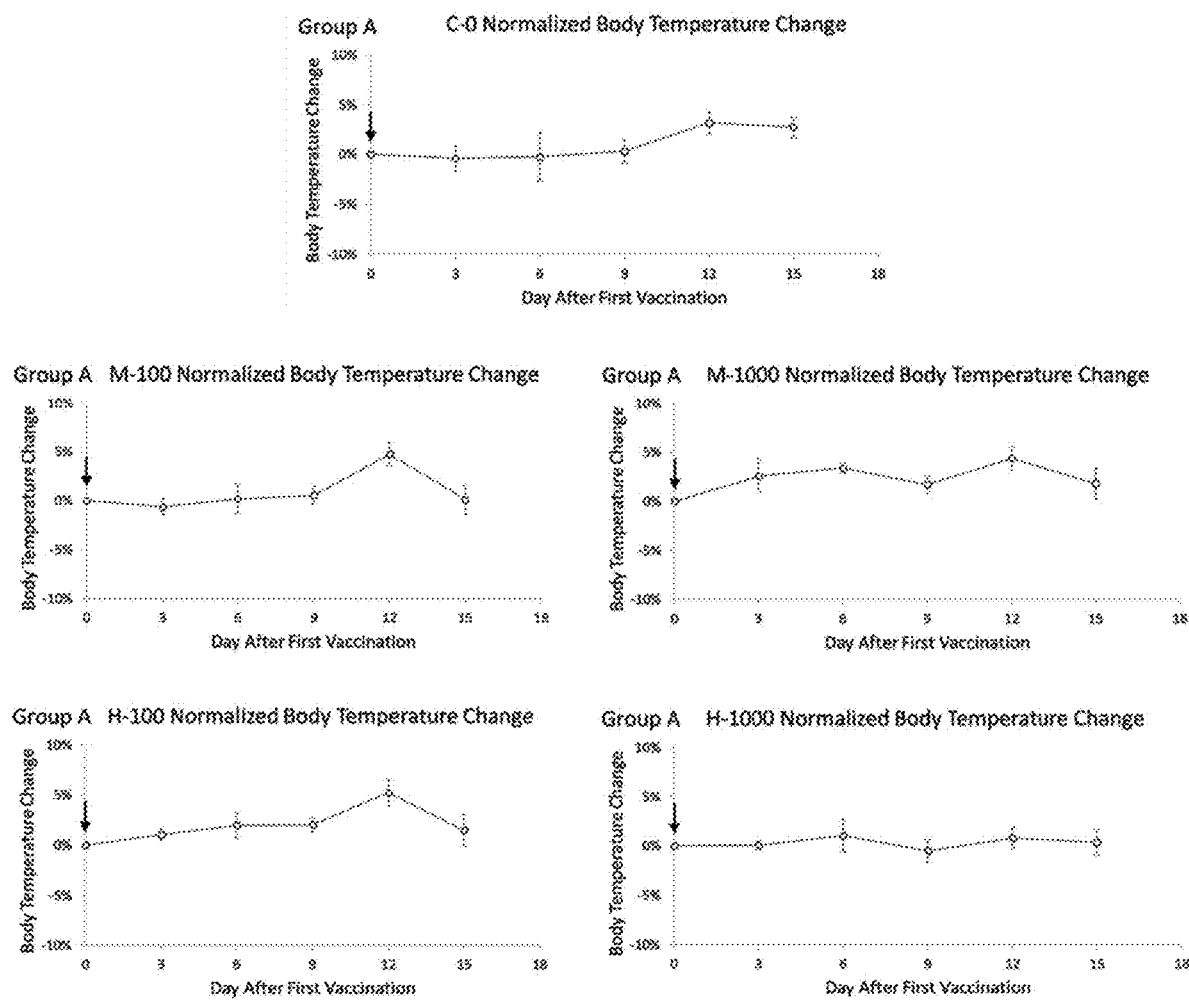
FIGS. 9-11 show changes in body temperatures from the time of first vaccination for the single vaccination group A mice (FIG. 9), the double vaccination group B mice (FIG. 10) and the triple vaccination group C mice (FIG. 11) in the toxicology study described in Example 5. Body temperature changes were normalized to the body temperature obtained on day 0 (set as 100%) and plotted as a percentage increase or decrease relative to this initial starting point. Temperatures were recorded at the same time of day for each mouse. Arrows indicate day(s) of vaccination. Error bars indicate ±SE.
Figure 10:
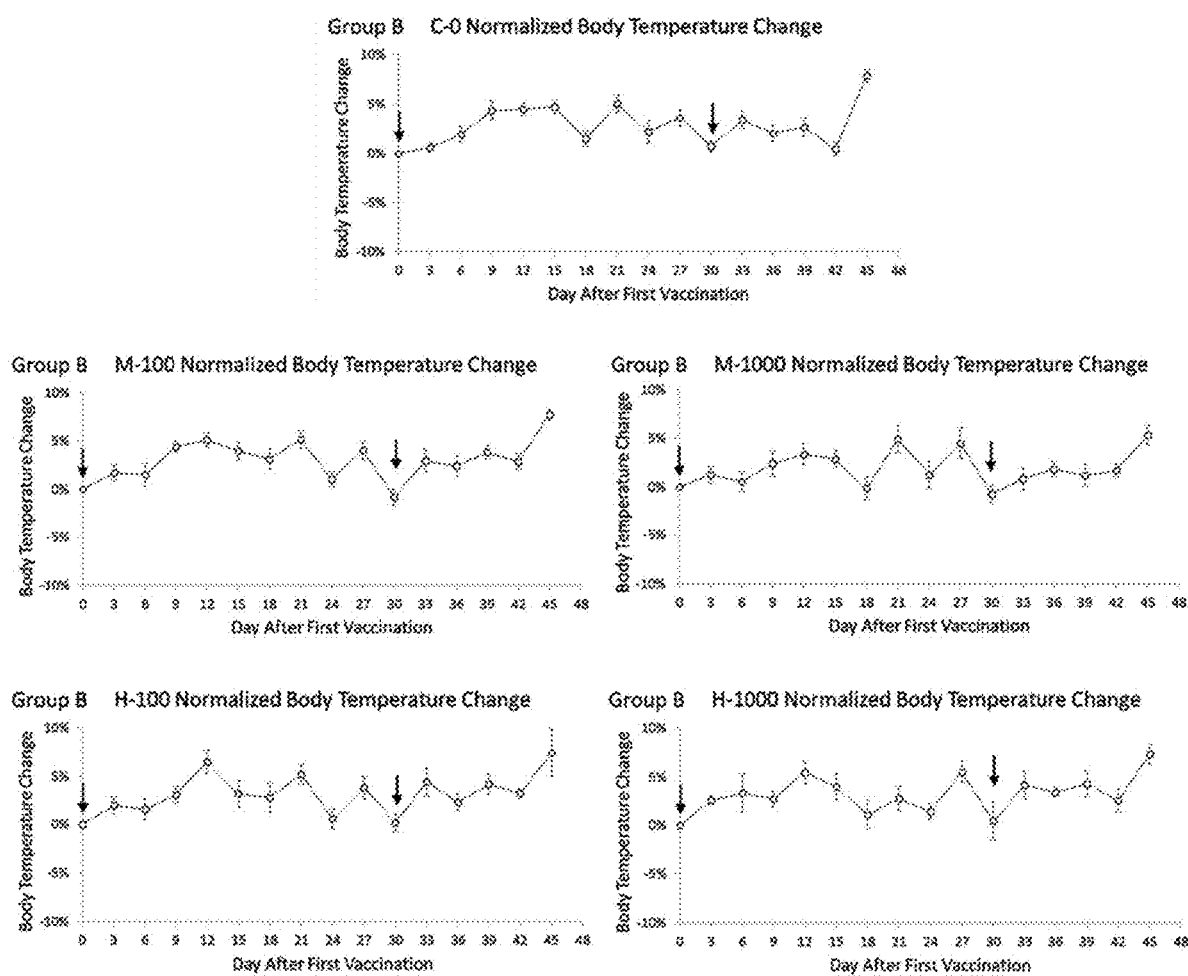
Figure 11:
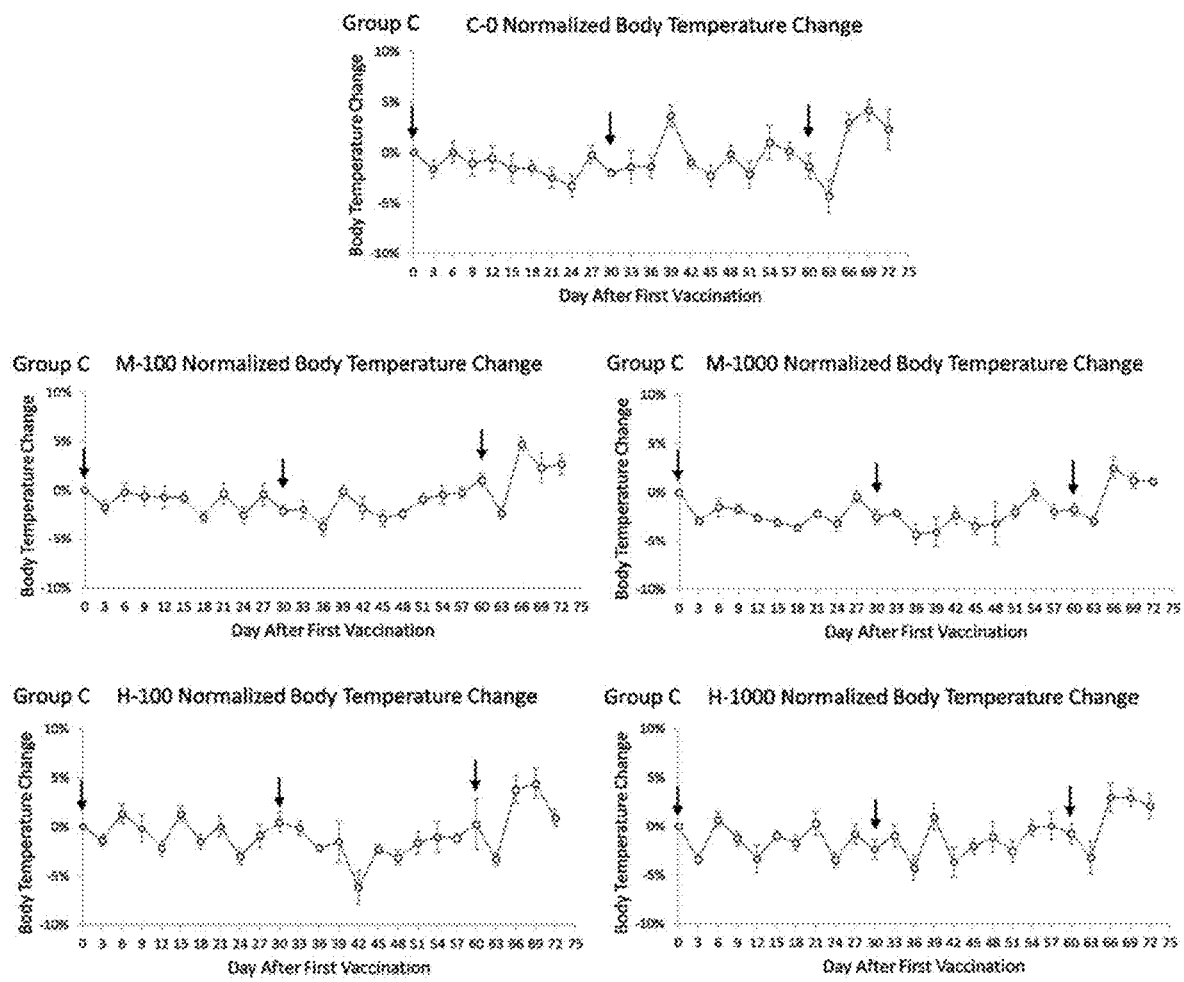
Figure 12:
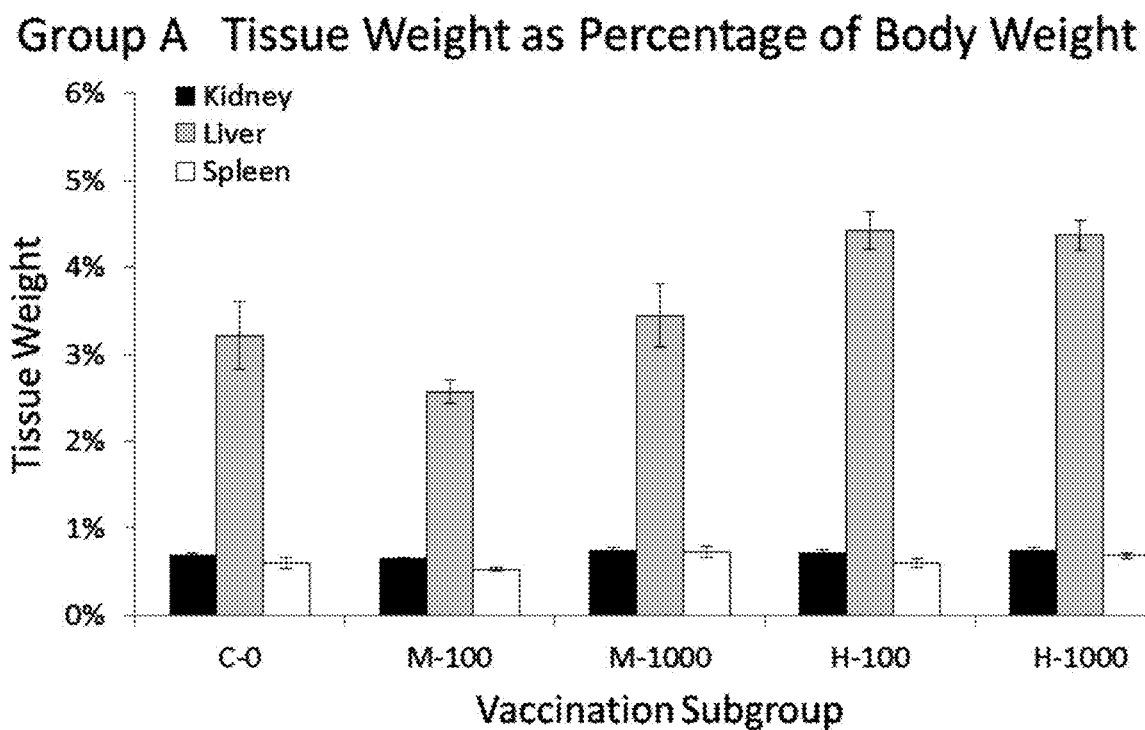
FIGS. 12-14 show the weights of the spleen, liver, and kidneys recorded at necropsy for the single vaccination group A mice (FIG. 12), the double vaccination group B mice (FIG. 13) and the triple vaccination group C mice (FIG. 15) in the toxicology study described in Example 5. Weights were expressed as a percentage of whole body weight, and mean percentages were plotted for each subgroup of mice (as delineated in Table 2, within Example 5). Error bars indicate ±SE.
Figure 13:
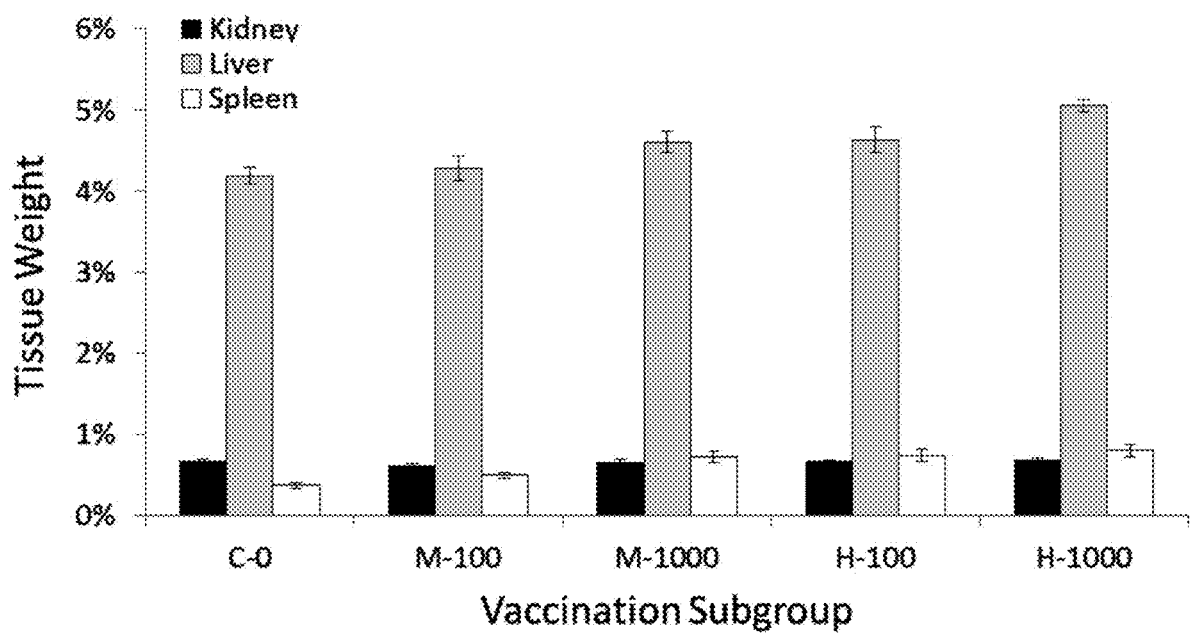
Figure 14:
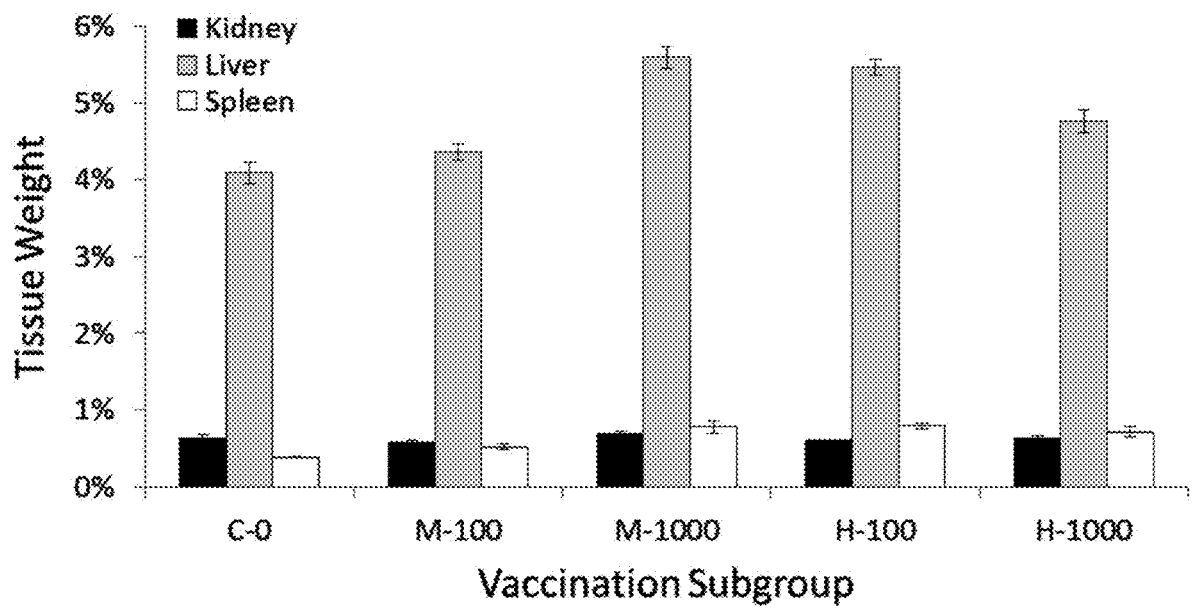

FIGS. 6-8 show body weight changes over the period of observation. FIGS. 9-11 show body temperature changes in each group and subgroup, and FIGS. 12-14 show weights of the spleen, liver, and kidneys recorded at the time of necropsy and expressed as a percentage of whole body weight.

No mortality or severe morbidity issues were grossly apparent during the entire study period. Morbidity seemed confined to the injection site, which did not completely heal or recover hair growth during the 14-15 days after the first dose or during the 45 or 75 day observation periods in mice receiving two or three doses, respectively. Overall, the mice showed normal behavior with respect to eating, drinking, and socializing. In general, mice gained weight over the course of the study, except for transient, slight dips in weight immediately following each vaccination, from which the mice recovered quickly. (See FIGS. 6-8.)

Mice receiving the highest doses of vaccine (M1000 and H1000) showed substantial interest in their injection sites 6 days after injection. The injection sites typically became hairless with a granulomatous appearance by day 9 and began to scab by day 12. By euthanasia at days 14-15 (for group A), scabs resolved, and the sites of injection appeared to be almost completely healed, though still hairless. This pattern of irritation, hair removal, scab formation, and healing resolution was also observed with second and third vaccinations in the M1000 and H1000 subgroups. For example, group B mice showed substantial healing from the first vaccination by the time the second vaccination was administered. Initial injection sites of mice receiving multiple doses showed continued improvement throughout the course of the study but did not show complete healing or complete return of hair growth during the 45-day observation period for mice receiving two doses or during the 75-day observation period for mice receiving three doses.

However, the extent of healing generally correlated with the age of the injection site, with oldest injection sites appearing most healthy. Conversely, the area of hair loss around injection sites was generally greater in the older injection sites. It is not clear why this occurred, but it may that the mice found it easier to scratch initial injection sites (which were closest to their heads).

Mice receiving three doses at the low dose of human α-lactalbumin (H100) but not mouse α-lactalbumin (M100) showed the same pattern of irritation, hair removal, scab formation, and healing resolution as mice injected with the highest vaccine doses. This aggressive response was confined to mice vaccinated with the human α-lactalbumin protein and appeared only after the third vaccination. Without wishing to be bound by any particular theory, the aggressive response in these mice may be related to the enhanced immunogenicity of the xenoantigen and the high level of immunity achieved against three doses of xenoantigens.

Figure 15:
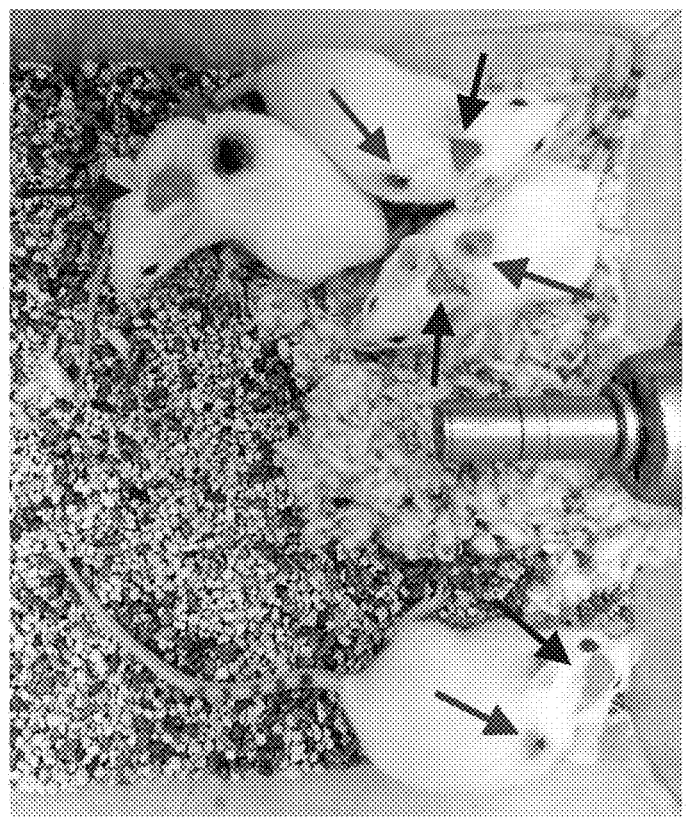
FIG. 15 shows representative appearances of immunization sites in mice who were subcutaneously administered zymosan/MONTANIDE™/α-lactalbumin emulsions, described further in Example 5.
Figure 16:
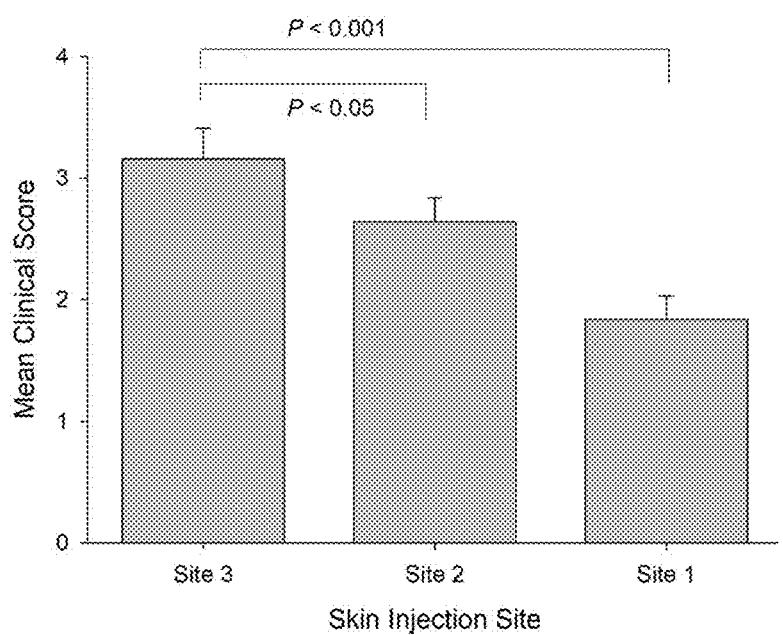
FIG. 16 depicts endpoint mean clinical scores of granulomas at three successive injection sites in BALB/c mice subcutaneously injected with zymosan/MONTANIDE™/α-lactalbumin emulsions, as described further in Example 5. Oil granulomas at the injection sites were commonly observed, and these were graded according to the following criteria: 0, normal; 1, minimal; 2, mild; 3, moderate; 4, severe. Means for all mice in all treatment groups (n=25) were calculated for each injection site. Error bars represent ±SE.

FIGS. 15 and 16 depict the resolution of granulomas at injection sites over time. FIG. 15 depicts photographs of mice taken approximately two weeks after a second injection and approximately 6 weeks after a first injection. Blue arrows indicate first injection sites, and red arrows indicate second injection sites. As FIG. 15 shows, first injection sites exhibited improved appearances relative to second injection sites, indicating resolution of granulomas over time.

FIG. 16 depicts mean grades for oil granulomas at injection sites, using the following grading system: 0, normal; 1, minimal; 2, mild; 3, moderate; 4, severe. Mean grades for all mice in all treatment groups (n=25) were calculated for each injection site. Error bars represent ±SE. All injection sites initially exhibited, on average, moderate oil granulomas. However, with time, these granulomas resolved substantially, with significant improvement evident between the first and third ($P<0.001$) and second and third ($P<0.05$) immunizations at the experimental endpoint.

Results from histopathological analyses of mice are shown in Tables 3A and 3B (group A; single dose), Tables 4A and 4B (group B; two doses), and Tables 5A-5C (group C; three doses). The following symbols were used in Tables 3A, 3B, 4A, 4B, 5A, 5B, and 5C:

n=normal (no lesions)
BI=biliary inflammation
FI=focus inflammation
OG=oil granuloma (injection site)
Ab=abscess
At=atrophy
GCH=germinal center hyperplasia LPH=lamina propria hyerplasia
MH=myeloid hyperplasia
em=epicardial mineralization
NP=nephropathy
FC=fatty change
FN=focal necrosis
u=ulcer
n/s=no section
ns=not seen
np=not present
Grades:
1=minimal
2=mild
3=moderate
4=severe In Group A (single dose) (Tables 3A and 3B), no adverse effects on organs were found in mice vaccinated with either human or mouse α-lactalbumin (M and H subgroups). Lesions were found at the injection sites; these were oil granulomas containing injected material, macrophages, and some neutrophils. In some mice, abscesses were found at the injection site. The abscesses suggest bacterial contamination of the injected material or occuring during the injection procedure. Most other lesions found were considered incidental because they were minimal to mild and were also found in the controls. Liver foci of inflammatory cells were observed in many mice and may have been related to injection site lesions.

TABLE 3A

Histopathological analysis of group A mice.

| Group A | Heart | Lung | Skin | Liver | Brain | Kidney | Bladder | Uterus |
|---|---|---|---|---|---|---|---|---|
| CO1 | n | n | OG2 | BI2 | n | n | n | n |
| CO2 | n | n | OG4 | FI1 | n | n | FI1 | n |
| CO3 | n | FI1 | OG2 | n | n | n | n | no ut |
| CO4 | n | n | OG3 | FI1 | n | n | n | n |
| CO5 | n | FI1 | OG4 | FI1 | n | n | FI1 | no ut |
| M100-1 | n | FI1 | OG1? | FI1 | n | n | n | fat |
| M100-2 | n | FI1 | OG3 | FI1 | n | n | n | n |
| M100-3 | n/s | n/s | n/s | FI1 | n | n | n | fat |
| M100-4 | n | n | OG4 | FI1 | FI1 | n | n | n |
| M100-5 | n | n | OG2 | FI1 | n | n | no epith | fat |
| M1000-1 | n | n | n | FI1 | n | n | no epith | n |
| M1000-2 | n | n | OG4 | FI2 | n | n | n | n |
| M1000-3 | FI1 | n | n | FI2 | n | n | n | n |
| M1000-4 | n | n | OG4 | FI1 | n | n | n | n |
| M1000-5 | n | n | n | FI1 | n | n | n | n |
| H100-1 | n | n | Ab4 | FI1 | n | n | n | n |
| H100-2 | n | n | n | FI1 | n | n | n | n |
| H100-3 | n | n | Ab4 | FI1 | n | n | no epith | n |
| H100-4 | n | n | n | FI1 | n | n | n | no ut |
| H100-5 | n | n | Ab4 | FI1 | n | n | n | n |
| H1000-1 | n | n | n | FI1 | n | n | n | n |
| H1000-2 | n | n | OG4 | FI1 | n | n | no epith | n |
| H1000-3 | n | FI1 | n | FI2 | n | n | no epith | n |
| H1000-4 | n | n | OG4, Ab4 | FI1 | n | n | n | n |
| H1000-5 | n | n | OG4 | FI2 | n | n | FI1 | n |

TABLE 3B

Histopathological analysis of group A mice.

| Group A | Ovary | Mam gland | Spleen | Large intestine | Small intestine | Stomach | Cecum | Thymus |
|---|---|---|---|---|---|---|---|---|
| CO1 | n/s | n | n | n | n | n/s | n | |
| CO2 | n | n | n | n | n | n | | |
| CO3 | n | n | n | n | n | n/s | n | |
| CO4 | n | n/s | n | n | n | n | | |
| CO5 | n | n | n | n | n | n/s | n | |
| M100-1 | n | n | n | n | n | n/s | n | |
| M100-2 | n | n | n | n | n | n | | |
| M100-3 | n | n | n | n | n | n/s | n | |
| M100-4 | n | n | n | n | n | n | | n |
| M100-5 | n | fat | n | n | n | n/s | n | |
| M1000-1 | n | n | n | n | n | n/s | n | |
| M1000-2 | n | n/s | n | n | n | n | | |
| M1000-3 | n | n | n | n | n | n | | |
| M1000-4 | n | n | At2 | n | LPH1? | n | | |
| M1000-5 | n | n | n | n | n | n | | |
| H100-1 | n | n/s | n | n | n | n | | |
| H100-2 | n | n | n | n | n | n | | |
| H100-3 | n | n | n | n | n | n | | |
| H100-4 | n | n | n | n | n | FI2 forestom | | |

TABLE 3B-continued

Histopathological analysis of group A mice.

| Group A | Ovary | Mam gland | Spleen | Large intestine | Small intestine | Stomach | Cecum | Thymus |
|---|---|---|---|---|---|---|---|---|
| H100-5 | n | n | n | n | n | n | | |
| H1000-1 | n | FI2 | GCH2 | n | LPH1? | n | | |
| H1000-2 | n | n | n | n | n | n | | |
| H1000-3 | n | n | GCH2 | n | n | n | | |
| H1000-4 | n | n/s | GCH1 | n | n | n | | |
| H1000-5 | n | n/s | n | n | n | n | | |

In Group B (two doses) (Tables 4A and 4B), liver foci of inflammatory cells were found in many mice. Liver foci were random and biliary and mostly composed of lymphocytes, sometimes with neutrophils and macrophages. Some liver foci were myeloid foci (myeloid hyperplasia in liver). Liver lesions included mild biliary inflammation and were likely not adverse for hepatocyte and liver function.

Splenic lesions of myeloid hyperplasia observed in some mice likely represented a reaction to injection site lesions.

Splenic lesions of germinal center hyperplasia observed in some mice could have been a reaction to the injection site lesions and/or a response to the antigen.

Mammary tissue was often in the skin section and not in the breast section, which often contained only muscle.

Abscesses were observed in some mice at the injection site and were composed of neutrophils, which may indicate a sterile abscess without bacteria or with bacteria. Bacteria were not usually seen in the lesions.

TABLE 4A

Histopathological analysis of group B mice.

| Group B | Heart | Lung | Skin 1 | Skin 2 | Liver | Brain | Kidney | Bladder | Uterus |
|---|---|---|---|---|---|---|---|---|---|
| CO1 | n | n | OG1 | OG4 | FI1 | n | n | no epith | n |
| CO2 | n | n | OG2 | OG4 | FI1 | n | n | n | fat |
| CO3 | n | n | n | OG4 | FI1 | n | n | n | n |
| CO4 | n | n | n | OG2 | FI1 | n | n | n | fat |
| CO5 | n | n | OG3 | n | FI1 | n | n | n | n |
| M100-1 | n | FI1 | OG4 | n | FI1 | n | n | no epith | n |
| M100-2 | n | n | OG1 | n | FI1 capsule | n | n | n | fat |
| M100-3 | n, em2 | n | OG4, Ab | OG4 | FI1 | n | n | n | n |
| M100-4 | n | n | n | n | FI2, FN1 | n | n | n | fat |
| M100-5 | n, em1 | n | OG4, Ab | OG4 | FI1 | n | n | n | n |
| M1000-1 | n | n | OG4 | OG4 | FI1 | n | n | n | n |
| M1000-2 | n, em2 | FI1 | n | OG2 | FI1 | n | n | n | n |
| M1000-3 | n | n | OG2 | OG3 | FI2 | n | n | n | n |
| M1000-4 | n, em1 | n | n | OG2 | FI2 | n | n | np | n |
| M1000-5 | n | FI1 | Inflam 3 | OG4 | FI2 | n | n | n | n |
| H100-1 | n | n | OG4 | OG4, Ab | FI1 | n | n | n | n |
| H100-2 | n | n | n | OG4 | FI2 | n | n | n | n |
| H100-3 | n | FI1 | OG2 | OG4 | FI1 | n | n | n | n |
| H100-4 | n | FI2 | OG4 | OG4, Ab | FI2 | n | n | n | n |
| H100-5 | n | n | OG4, Ab | OG4, Ab | FI1 | n | n | n | n |
| H1000-1 | n | n | OG4 | n | FI1 | n | n | n | n |
| H1000-2 | n | n | OG3 | OG4, u | FI2 | n | n | n | n |
| H1000-3 | n | n | OG3 | OG4, u | FI2 | n | n | n | n |
| H1000-4 | n | n | OG2 | OG4 | FI2 | n | n | n | n |
| H1000-5 | n | n | OG2 | OG4 | FI1 | n | n | n | n |

TABLE 4B

Histopathological analysis of group B mice.

| Group B | Ovary | Mam. gland | Spleen | Large intest. | Small intest. | Stomach | Cecum |
|---|---|---|---|---|---|---|---|
| CO1 | n | n | n | n | n | n | |
| CO2 | n | n | n | n | n | n/s | n |
| CO3 | n | n | n | n | n | n | |
| CO4 | n | n | n | n | n | n | |
| CO5 | n | n | n | n | n | n | |
| M100-1 | n | n | n | n | n | n | |
| M100-2 | n | n | n | n | n | FI1 serosa | |
| M100-3 | n | n | n | n | n | n | |
| M100-4 | n | n | n | n | n | n | |
| M100-5 | n | n | n | n | n | n | |

TABLE 4B-continued

Histopathological analysis of group B mice.

| Group B | Ovary | Mam. gland | Spleen | Large intest. | Small intest. | Stomach | Cecum |
|---|---|---|---|---|---|---|---|
| M1000-1 | n | n | MH2 | n | n | n | |
| M1000-2 | n | n | GCH1, MH1 | n | n | n | |
| M1000-3 | n | n | GCH1, MH1 | n | n | n | |
| M1000-4 | n | n | MH1 | n | n | n | |
| M1000-5 | n | n | GCH1, MH1 | n | n | n | |
| H100-1 | n | n | n | n | n | n | |
| H100-2 | n | n | GCH1, MH1 | n | n | n | |
| H100-3 | n | n | n | n | n | n | |
| H100-4 | n | n | MH1 | n | n | n | |
| H100-5 | n | n | n | n | n | n | |
| H1000-1 | n | n | GCH1, MH2 | n | n | n | |
| H1000-2 | n | n | GCH1, MH2 | n | n | n | |
| H1000-3 | n | n | GCH1, MH1 | n | n | n | |
| H1000-4 | n | n | MH1 | n | n | n | |
| H1000-5 | n | n | GCH1, MH1 | n | n | n | |

In Group C (three doses) (Tables 5A-5C), histopathology results were similar to those of Groups A and B. The most severe skin lesions were in the third (most recent) injection site. No organ-specific toxic lesions were observed. Most of the observed lesions that were not associated with dose were incidental lesions.

Liver lesions were also most severe in high dose mice. These lesions resembled those caused by *Helicobacter hepaticus*, which is common in immunodeficient mice. To evaluate the cause of these liver lesions, livers of three mice with many hepatic foci of inflammation, which contained infiltrates comprising mostly lymphocytes and some macrophages with occasional necrosis) were stained by the Steiner stein. Also included was a positive control section of human stomach in which bacteria was present. None of the mouse livers with inflammatory loci had lesions that stained positive for bacteria. Therefore, the liver lesions observed in those mice were not likely due to infection with *Helicobacter hepaticus*.

TABLE 5A

Histopathological analysis of group C mice.

| Group C | Heart | Lung | Skin 1 | Skin 2 | Skin 3 | Liver | Brain | Kidney |
|---|---|---|---|---|---|---|---|---|
| CO1 | n | n | OG2 | OG2 | OG4 | FI1 | n | NP1 |
| CO2 | em1 | n | OG3 | OG3 | OG4 | FI1 | n | n |
| CO3 | n | n | n | OG2 | OG1 | n | n | FC1 |
| CO4 | n | n | n | OG3 | OG3 | FI1 | n | n |
| CO5 | n | n | OG3 | OG4 | OG2 | FI1 | n | n |
| M100-1 | n | FI1 | OG3 | OG4 | OG4 | FI1 | n | n |
| M100-2 | n | n | OG3 | OG3 | OG4 | FI2 | n | n |
| M100-3 | n | n | OG3 | OG4 | OG3 | FI1 | n | n |
| M100-4 | n | n | OG1 | OG4 | n | FI1 | n | n |
| M100-5 | n | n | OG1 | OG3 | OG3 | FI1 | n | n |
| M1000-1 | n | n | OG3 | OG1 | OG3 | FI2 | n | n |
| M1000-2 | n | FI1 | OG2 | OG2 | OG2 | FI3 | n | n |
| M1000-3 | n | FI1 | OG1 | OG4 | OG3 | FI3 | n | n |
| M1000-4 | em1 | n | OG2 | OG2 | OG4 | FI2 | n | n |
| M1000-5 | n | FI1 | OG1 | OG3 | n | FI2 | n | n |
| H100-1 | n | n | OG2 | OG2 | OG4 | FI2 | n | n |
| H100-2 | n | FI1 | OG3 | OG2 | OG4 | FI2 | n | n |
| H100-3 | n | FI1 | OG2 | OG1 | OG4 | FI3 | n | n |
| H100-4 | n | n | OG2 | OG1 | OG3 | FI3 | n | n |
| H100-5 | n | FI1 | OG1 | OG2 | OG4 | FI2 | n | n |
| H1000-1 | n | FI1 | OG1 | OG4 | OG4, Ab | FI3 | n | n |
| H1000-2 | n | FI1 | OG2 | OG3 | OG4, Ab | FI2 | n | n |
| H1000-3 | n | n | OG2 | OG2 | OG4 | FI2 | n | n |
| H1000-4 | n | FI1 | OG2 | OG3 | OG4, Ab | FI3 | n | n |
| H1000-5 | n | n | OG1 | OG2 | OG4 | Fi3 | n | n |

TABLE 5B

Histopathological analysis of group C mice.

| Group C | Bladder | Uterus | Ovary | Mam. gland | Spleen | Large intest. | Small intest. |
|---|---|---|---|---|---|---|---|
| CO1 | n | n | n | n | n | n | n |
| CO2 | n | n | n | n | n | n | n |

TABLE 5B-continued

Histopathological analysis of group C mice.

| Group C | Bladder | Uterus | Ovary | Mam. gland | Spleen | Large intest. | Small intest. |
|---|---|---|---|---|---|---|---|
| CO3 | n | n | n | FI1 | At2 | n | n |
| CO4 | n | n | n | n | n | n | n |
| CO5 | FI2 | n | n | n | n | n | n |
| M100-1 | n | n | n | n | MH1 | n | n |
| M100-2 | n | n | n | n | MH1 | n | n |
| M100-3 | n | n | n | n | MH1 | n | n |
| M100-4 | n | n | n | n | MH1 | n | n |
| M100-5 | n | n | n | n | n | n | n |
| M1000-1 | np | n | n | n | MH2 | n | n |
| M1000-2 | n | n | n | n | MH3 | n | n |
| M1000-3 | n | n | n | n | MH2 | n | n |
| M1000-4 | n | n | n | n | GCH1, MH3 | n | n |
| M1000-5 | n | n | n | n | MH2 | n | n |
| H100-1 | n | n | n | n | MH2 | n | n |
| H100-2 | n | n | n | n | MH2 | n | n |
| H100-3 | n | n | n | n | MH2 | n | n |
| H100-4 | n | n | n | n | MH2 | n | n |
| H100-5 | n | n | n | n | MH1 | n | n |
| H1000-1 | n | n | n | n | GCH1, MH1 | n | n |
| H1000-2 | n | n | n | n | MH1 | n | n |
| H1000-3 | n | n | n | n | MH1 | n | n |
| H1000-4 | n | n | n | n | MH1 | n | n |
| H1000-5 | n | n | n | n | GCH1, MH1 | n | n |

TABLE 5C

Histopathological analysis of group C mice.

| Group C | Stomach | Pancreas | Salivary gland | Thymus | Mesenteric lymph nodes |
|---|---|---|---|---|---|
| CO1 | n | ns | ns | n | n |
| CO2 | n | n | n | n | n |
| CO3 | n | n | n | n | piece n |
| CO4 | n | n | n | n | n |
| CO5 | n | n | n | n | n |
| M100-1 | n | n | n | n | n |
| M100-2 | n | np | np | n | n |
| M100-3 | n | n | n | n | n |
| M100-4 | n | np | n | n | n |
| M100-5 | n | n | n | n | n |
| M1000-1 | n | np | n | n | n |
| M1000-2 | n | n | n | n | n |
| M1000-3 | n | np | np | n | np |
| M1000-4 | n | n | n | n | n |
| M1000-5 | n | np | np | n | n |
| H100-1 | n | np | n | n | n |
| H100-2 | n | n | n | n | n |
| H100-3 | n | n | n | n | n |
| H100-4 | n | n | n | n | n |
| H100-5 | n | np | np | n | n |
| H1000-1 | n | n | n | n | n |
| H1000-2 | n | ns | n | n | n |
| H1000-3 | n | n | FI1 | n | n |
| H1000-4 | FI1 | n | n | n | n |
| H1000-5 | n | n | n | n | n |

Figure 17:
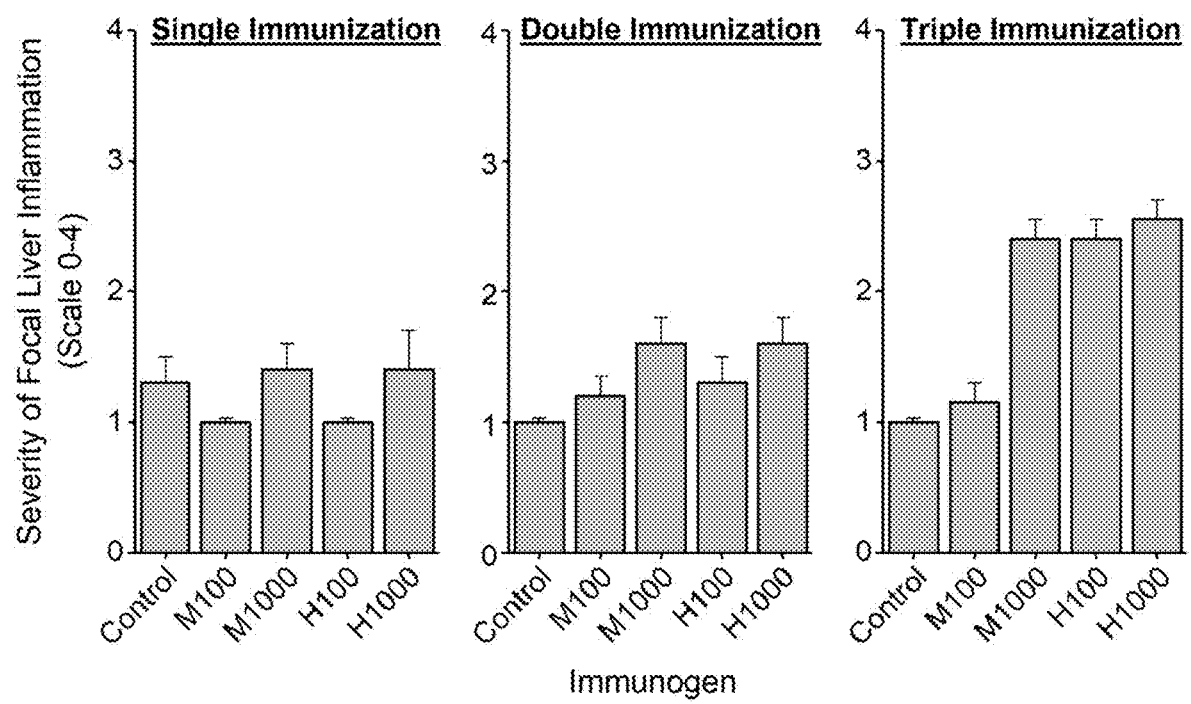
FIG. 17 presents a summary of the severity of focal liver inflammations in all groups in the toxicology study described in Example 5.

FIG. 17 presents a summary of the severity of focal liver inflammations in all groups.

In summary, these results indicate that the liver foci were random, focal, biliary, and predominantly mild and benign with the most severe lesions occurring in the high dose mice. The liver foci were likely non-adverse for hepatocyte and liver function.

Example 6: Prophylactic Inhibition of Autochthonous Breast Cancer Growth by Immunization with α-Lactalbumin/Zymosan/MONTANIDE™

MMTV-neu mice can be used as a mouse model of autochthonous breast cancer. MMTV-neu mice express a neu protooncogene under the regulation of the long terminal repeat of mouse mammary tumor virus (MMTV) and develop spontaneous mammary tumors, with a 50% incidence by 205 days of age. (See, e.g., Guy C T, et al. Expression of the neu protooncogene in the mammary epithelium of transgenic mice induces metastatic disease. *Proc Natl Acad Sci USA*. 1992; 89:10578-10582.)

To test the ability of α-lactalbumin/zymosan/MONTANIDE™ vaccines to inhibit breast cancer growth, MMTV-neu mice are administered three or more doses containing α-lactalbumin in zymosan and Montanide, e.g., at a dose of 1000 μg each of zymosan and Montanide. Additional groups of mice may be used as controls or for comparison and may include mice that each receive doses of: 1) α-lactalbumin in CFA (positive control); 2) α-lactalbumin in zymosan and IFA; or 3) zymosan in MONTANIDE™ with no antigen (negative control).

To evaluate the ability of α-lactalbumin/zymosan/MONTANIDE™ vaccines to inhibit cancer growth before they appear, the first, second, and third doses may all be administered well before the mice are expected to develop tumors, e.g., at 6-10 weeks. Tumor incidences and/or sizes are examined and compared between groups.

Example 7: Inhibition of Established Breast Cancer Growth by Immunization with α-Lactalbumin/Zymosan/Montanide To test the ability of α-lactalbumin/zymosan/MONTANIDE™ vaccines to inhibit further growth of already established breast cancers, mice from one or more suitable cancer models are administered three or more doses containing α-lactalbumin in zymosan and MONTANIDE™, e.g., at a dose of 1000 μg each of zymosan and MONTANIDE™. Experiments and mouse groupings are similar to those described in Example 4, except that the doses may be timed differently depending on the cancer model. For example, at least one, two, or three doses are administered to mice at a certain age at which, according to known characteristics of the mouse model, a substantial proportion of mice in that cancer model will already have established cancers. Alternatively, at least one, two or three doses are administered after the mouse exhibits at least one sign of having developed at least one tumor, e.g., the mouse has at least one palpable tumor.

Any of a variety of suitable cancer models can be used to test effects on established breast tumors include. By way of a non-limiting example, MMTV-PyVT transgenic mice constitutively express an activated form of the neu oncogene in breast tissues and develop aggressive palpable mammary tumors by 5 weeks of age. (See, e.g., Guy C T, Cardiff R D, Muller W J. Induction of mammary tumors by expression of polyomavirus middle T oncogene: a transgenic mouse model for metastatic disease. *Mol Cell Biol.* 1992; 12:954-961.) Thus, MMTV-PyVT mice can be used to evaluate effects on autochthonous tumor growth.

Transplantable breast cancer models may also be suitable. For example, mice may be inoculated by injection with tumor cells of a mammary carcinoma cell line such as 4T1.

Tumor sizes at one or more distinct timepoints (e.g., time after immunization, time after tumor cell inoculation, etc.) are examined and compared between groups.

Example 8: Phase I Clinical Trial of an α-Lactalbumin Vaccine in Patients with Non-Metastatic Triple-Negative Breast Cancer at High Risk of Recurrence Treatment of triple-negative breast cancer is inadequate and hampered by the absence of actionable therapeutic targets. Results described in Examples 2-4 and results from other pre-clinical studies suggest that a vaccine comprising α-lactalbumin (antigen) and zymosan (in a MONTANIDE™ vehicle) can induce an immune response consistent with effective prevention and treatment of breast tumors. Moreover, this vaccine has great potential to treat human triple-negative breast cancer.

An open-label, phase I clinical trial is planned to determine the dose and schedule of the vaccine to be used in future trials. This trial includes an initial dose-escalating phase to determine the maximum tolerated dose (MTD) of an α-lactalbumin/zymosan/MONTANIDE™ vaccine in patients with non-metastatic triple-negative breast cancer (TNBC). Thereafter, cohort expansion is used to explore the relationship between vaccine dose and immunologic response in order to select a dose for a Phase II trial.

Figure 18:
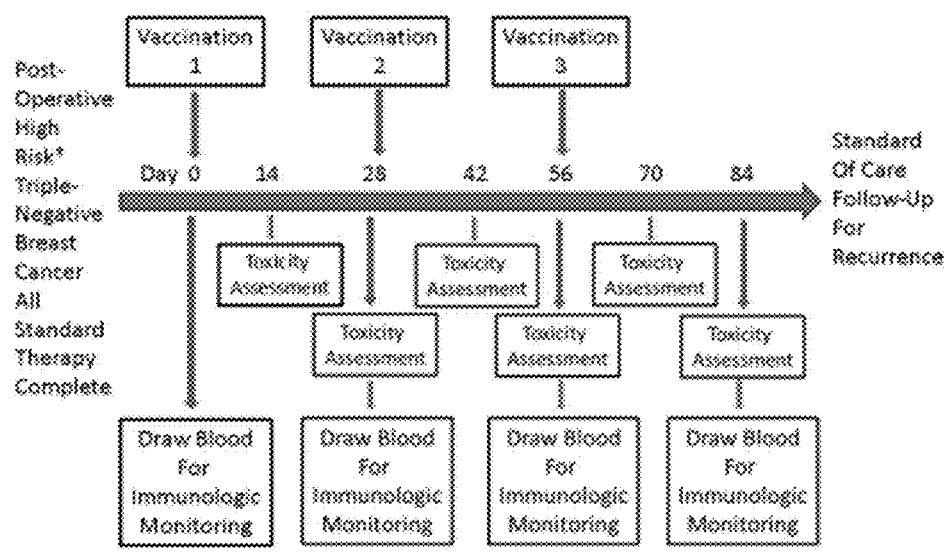
FIG. 18 shows a study scheme for the clinical trial described in Example 8. The scheme indicates a timeline for dose administrations, toxicity assessments, and blood draws for immunologic monitoring.

FIG. 18 shows a study scheme indicating a timeline for dose administrations, toxicity assessments, and blood draws for immunologic monitoring.

Objectives and Endpoints

Primary objective: Determine the Maximum Tolerated Dose (MTD) of an α-lactalbumin/zymosan/MONTANIDE™ vaccine in patients with non-metastatic TNBC.

Secondary objective: measure the immune response to the vaccine, focusing on the ability to induce a proinflammatory T cell response consistent with tumor protection. This assessment is determined using an ELISPOT assay to determine peripheral blood frequencies of T cells that produce interferon-gamma (IFNγ; type-1) and IL-17 (type-17) in response to recombinant human α-lactalbumin. Based on these immunologic assays, the lowest dose which produces an immunologic effect—the Lowest Immunologic Dose (LID)—is identified.

An immunologic response is defined as the post-treatment development of $1/30,000$ IFNγ-secreting (type 1) and/or IL-17 secreting (type 17) T cells elicited from peripheral blood mononuclear cells in response to α-lactalbumin/zymosan/MONTANIDE™ vaccination The LID is defined as the lowest tolerable dose at which an immunologic response was seen in >1/10 patients.

Exploratory objective: Determine the Optimal Immunologic Dose (OID) of α-lactalbumin vaccine in a population of patients with operable TNBC, based on ELISPOT assays. The OID is defined as the dose at which most of the patients developed an immune response as defined above. If more than one dose level has the same number of immune responders, the lowest of these dose-levels is defined as the OID. The OID must be <the MTD.

Correlative objectives:
Examine the cellular response to α-lactalbumin/zymosan/MONTANIDE™ vaccination in a population of patients with operable TNBC using ELISPOT assays of IFNγ and IL-17 production in response to α-lactalbumin stimulation.
Examine the humoral response to α-lactalbumin/zymosan/MONTANIDE™ vaccination in a population of patients with operable TNBC, using an ELISA assay.

Safety objective: Determine incidence of adverse events (drug related and treatment emergent).

Subjects

Between 40 and 60 subjects meeting the inclusion criteria below but not excluded by any of the exclusion criteria below are enrolled. These subjects represent a high-risk population having operable TNBC. Subjects are enrolled following completion of all standard therapy, which may include chemotherapy, surgery, or radiation. Chemotherapy may be given either pre- or post-operatively.

Inclusion criteria: The trial is open to both men and women and to members of all races and ethnic groups. A potential subject must meet all of the following inclusion criteria to be eligible for enrollment:

Histologically proven invasive breast cancer
Primary tumor is estrogen receptor (ER)-negative (ER in <1% of cells), progesterone receptor (PR)-negative (PR in <1% of cells), and HER2-negative (0-1+ by IHC or FISH ratio <2.0 with signal number <6/cell) ("triple-negative breast cancer").
High risk, defined as either
  pathologic stage IIA, IIB, IIIA, IIIB, or IIIC by AJCC 6, or
  residual invasive cancer in breast or regional nodes following pre-operative chemotherapy
Six months or less since last active therapy (chemotherapy, radiation therapy, or surgery) and <12 months since the initiation of treatment for the current cancer.
Treatment prior to enrollment must be consistent with contemporary NCCN guidelines, found at the website found at the address "https://" followed immediately by "www.nccn.org/"
Age >18 years
ECOG (Eastern Performancy Oncology Group) Performance Status 0-1. (See, e.g., Oken M, Creech R, Tormey D, et al. Toxicity and response criteria of the Eastern Cooperative Oncology Group. *Am J Clin Oncol.* 1982; 5:649-655; or the website found at the address "https://" followed immediately by "ecog-acrin.org/resources/ecog-performance-status").

Adequate major organ function, defined as WBC >3,000/ mcl; hemoglobin >10.0 gm/dL, platelets >100,000/ mcL, total bilirubin within normal limits, ALT/ AST<2.5×upper limits of normal (ULN), and serum creatinine<1.5×ULN Serum prolactin level must be <upper limits of normal (ULN)

Ability to understand and the willingness to sign and provide a written informed consent document Archival tissue is available for potential correlative studies (e.g., assays for α-lactalbumin expression or Tumor Infiltrating Lymphocytes), but tumors will not be required to exhibit overexpression of α-lactalbumin for enrollment.

Subject agrees not to use alternative therapies from the time of informed consent through 30 days following the last vaccine injection.

Exclusion criteria. Any of the following characteristics will exclude a potential subject from this study:

Receipt of cytotoxic chemotherapy within 4 weeks of study entry

Radiation therapy within 4 weeks of study entry

Failure to recover from the toxicity of the previous therapy to the National Cancer Institute's Common Terminology Criteria for Adverse Events (CTCAE) Grade 0-1, except for alopecia and grade 2 neuropathy.

Need for systemic corticosteroid use (except as physiologic replacement, defined as prednisone 10 mg/day or equivalent).

Need for immunosuppression (e.g., for a history of organ transplantation)

Known HIV infection

Active or planned lactation or pregnancy

Taking or planning to take oral contraceptives

Refusal to use effective non-hormonal contraception. Acceptable contraception methods include but may not be limited to barrier contraception (diaphragm or condom), non-hormonal intrauterine device, and vasectomy of male partner.

Receipt of any other investigational agents within the last 4 weeks.

Any known recurrence or metastasis

History of another active invasive malignancy within 5 years of study entry

History of allergic reactions to α-lactalbumin, human milk (excluding lactose intolerance), zymosan, or other agents used in this study Uncontrolled intercurrent illness including, but not limited to, ongoing or active infection, symptomatic congestive heart failure, unstable angina pectoris, cardiac arrhythmia, or psychiatric illness/social situations that would limit compliance with study requirements Known hyperprolactinemia Current treatment with drugs known to cause hyperprolactinemia Known allergy to penicillin Subject Screening Subjects are screened by review of medical records, history, and physical exam. Pathology material determining study eligibility are also reviewed. Screening is performed within 4 weeks before administration of the first vaccination.

Consenting potentially-eligible subjects undergo laboratory testing, including complete blood count (CBC) with differential, prolactin level, and comprehensive metabolic profile (total protein, albumin, calcium, total bilirubin, alkaline phosphatase, AST, glucose, BUN, creatinine, sodium, potassium, chloride, bicarbonate, and ALT), and pregnancy test.

Subjects are not required to undergo scans to exclude metastatic disease but will be managed according to American Society of Clinical Oncology (ASCO) and National Comprehensive Cancer Network (NCCN) guidelines. Potential study subjects with signs or symptoms of metastatic disease or with unexplained abnormal alkaline phosphatase or liver function tests will undergo standard-of-care imaging to exclude the presence of metastases.

Vaccine Formulations cGMP-grade zymosan A (Sigma-Aldrich Fine Chemicals, Buchs, Switzerland) is suspended in GMP-grade MONTANIDE™ ISA 51 VG (Seppic, Fairfield, N.J.) to make a zymosan/MONTANIDE™ suspension. MONTANIDE™ ISA 51 VG is a light mineral oil/surfactant solvent that facilitates creation of water-in-oil emulsions and has much greater metabolizability than the incomplete Freund's adjuvant (IFA) oil used in to formulate CFA. GMP-grade recombinant human α-lactalbumin (rhαlac) (List Biologicals, Campbell, Calif.) in USP grade $H_2O$ is mixed with the zymosan/MONTANIDE™ suspension to generate a water-in-oil emulsion. Each emulsion preparation is made by a clinical pharmacist on the day of its use and is administered to each patient within 2 hours of its release.

Dosing and Administration

Subjects are administered α-lactalbumin/zymosan/MONTANIDE™ vaccines by subcutaneous administration in rotating sites (left thigh, right thigh, and abdomen). Subjects receive three doses spaced four weeks apart. In the initial dose-escalating phase, patients are enrolled sequentially into 1 of 6 different dose levels (as shown in Table 6) each comprised of cohorts of 1-6 patients until the MTD has been identified. Dose level 1 is 1% of the dose routinely given to mice in previous pre-clinical studies. Intra-patient dose escalation is not permitted.

TABLE 6

Dose levels for dose escalation study

| Dose Level | Number of Patients | Dose of Vaccine | Dose of zymosan | Day 0 | Day 28 | Day 56 |
|---|---|---|---|---|---|---|
| 1 | 1-10 | 1 mcg | 1 mcg | X | X | X |
| 2 | 1-10 | 10 mcg | 10 mcg | X | X | X |
| 3 | 1-10 | 100 mcg | 100 mcg | X | X | X |
| 4 | 1-10 | 250 mcg | 250 mcg | X | X | X |
| 5 | 1-10 | 500 mcg | 500 mcg | X | X | X |
| 6 | 1-10 | 1000 mcg | 1000 mcg | X | X | X | mcg = microgram

MONTANIDE™ is used as a solvent at all dose levels.

Dose escalation proceeds within each cohort according to the accelerated titration dose-escalatoin scheme summarized in Table 7. Dose-limiting toxicity (DLT) generally corresponds to CTCAE version 5 Grade 2 or greater toxicity. (CTCAE version 5 may be found at the website whose address is https:// followed immediately by "ctep.cancer.gov/protocolDevelopment/electronic_applications/docs/CTCAE_v5_Quick_Reference_8.5x11.pdf") Once a grade 1 toxicity is noted, the dose escalation scheme presented in Table 8 is used.

TABLE 7

Accelerated titration dose-escalation scheme

| Toxicity observed at a Given Dose Level | Escalation Decision Rule |
| --- | --- |
| No toxicity | Enter 1 subject at the next dose level. |
| Grade 1 or 2 toxicity | Switch to standard "3 + 3" at this level, following the schema in Table 8 |
| Grade 3 or higher toxicity | Stop escalation; MTD exceeded; expand the next lower dose level to 6 subjects |

TABLE 8

Dose escalation scheme once grade 1 toxicity is noted.

| Number of Subjects with DLT (Grade 2) at a Given Dose Level | Escalation Decision Rule |
| --- | --- |
| 0 out of 3 | Enter 3 subjects at the next dose level. |
| 1 grade 2 out of 3 subjects With no grade ≥3 toxicity | Enter 3 more subjects at this dose level. If 0 of these 3 subjects experience DLT, enroll subsequent patients at the next higher dose level. If 1 or more of this group suffer DLT, then stop dose escalation, and declare the next lower dose level the MTD. Expand the next lower dose level to 6 if less than 6 subjects were treated previously at that dose. |
| ≥2 grade 2 out of 3 subjects or ≥1 grade 3 | Stop dose escalation. Declare the next lower dose level the MTD. Expand the next lower dose level to 6 if less than 6 subjects were treated previously at that dose. |
| ≤1 grade 2 out of 6 subjects | This is generally the recommended MTD. To identify the LID and/or OID and further confirm safety, additional subjects are entered to a maximum of 10. |

Once the MTD is identified, the dose-level expansion phase begins. The MTD is expanded to 10 subjects, and immunologic correlative studies are performed in all 10 subjects. Table 9 outlines a scheme for the dose expansion phase.

TABLE 9

Dose expansion phase scheme (once MTD is identified and expanded to 10 subjects)

| Number of Subjects with Grade 2 DLT (no Grade 3) at a Given Dose Level | Expansion Decision Rules | Immunologic Response Seen in ≥1/10 patients? | Action |
| --- | --- | --- | --- |
| 0-1/3-6 or 0/2 | Expand current dose level to 10 patients. If a total of ≥3/10 patients at this dose level develop DLTs, the next lower dose level is declared the new MTD | (Dose is not considered in the determination of the LID or OID) | |
| 0-2/10 | Dose level is considered tolerable. | Yes | May or may not be the LID. Proceed to next lower dose. |
| 0-2/10 | Dose level is considered tolerable. | No | The next higher dose is considered the LID |

After expansion of the MTD, successively lower doses are expanded to 10 patients until the lowest dose level associated with an immune response has been expanded.

Assessments

Subjects are assessed according to the study calendar presented in Table 10. Subjects undergo a history and physical exam (including breast exam) at screening, Day 0, every 4 weeks, and at the Day 84 visit.

Subjects are evaluated for toxicity for 4 weeks after the last vaccination, or until resolution of all toxicity to grade 0-1, whichever is later. All patients are contacted or seen in long-term follow-up to allow long-term monitoring for toxicity, relapse and survival.

Any subject receiving at least one vaccination as part of this trial is considered evaluable for toxicity. In order to allow safe dose-escalation, subjects withdrawing from treatment before receiving 3 doses of the investigational vaccine in the absence of a dose-limiting toxicity (DLT) are replaced. Subjects who develop any DLT after any number of doses are considered fully evaluable and are not replaced, even if no correlative immunologic studies are performed.

TABLE 10

Study calendar

| Action | Pre-Study[1] | Day 0 | Day 14[2] | Day 28[2] | Day 42[2] | Day 56[2] | Day 70[2] | Day 84[2] or off study |
| --- | --- | --- | --- | --- | --- | --- | --- | --- |
| Informed Consent | X | | | | | | | |
| History and Physical Exam, including breast exam | X | X | | X | | X | | X |
| Toxicity Assessment | | X | X | X | X | X | X | X |
| CBC w/Differential and CMP[3] | X | | X | X | X | X | X | X |
| Prolactin Level | X | | | | | | | |
| Serum Pregnancy Test | X | | | | | | | |
| Serum α-lactalbumin ELISA | X | | | | | | | |

TABLE 10-continued

Study calendar

| Action | Pre-Study[1] | Day 0 | Day 14[2] | Day 28[2] | Day 42[2] | Day 56[2] | Day 70[2] | Day 84[2] or off study |
|---|---|---|---|---|---|---|---|---|
| Immunologic Monitoring[4] | | X | | X | | X | | X |
| Vaccination[5] | | X[5] | | X[5] | | X[5] | | |
| Vital Signs[6] | | X[6] | | X[6] | | X[6] | | |

[1]Screening visits occur within 28 days of the Day 0 visit. Scans are not required to exclude metastatic disease.
[2]All visits +/−3 working days.
[3]CMP (Comprehensive Metabolic Profile) includes total protein, albumin, calcium, total bilirubin, alkaline phosphatase, AST, glucose, BUN, creatinine, sodium, potassium, chloride, bicarbonate, anion gap, and ALT.
[4]ELISPOT frequencies of α-lactalbumin and ovalbumin specific T cells; culture supernatant levels of IFNγ and IL-17 flow cytometry determination of central vs. effector memory T cell percentages; and direct ELISA measurement of α-lactalbumin antibody titers.
[5]Allow ≥2 hours for vaccine preparation
[6]Following administration of the vaccine, vital signs are taken every 15 minutes for 60 minutes, and again at 120 minutes. Patient are observed for 120 minutes.

Example 9: Vaccine Formulations Comprising Zymosan Suspended in MONTANIDE™

Other vaccine formulations comprising an adjuvant as disclosed herein may be generated and tested in accordance with the present invention. For example, any antigen of interest, e.g., a polypeptide antigen, may be mixed with zymosan suspended in MONTANIDE™. An antigen of interest may be expressed, e.g., on tumor cells and/or pathogenic organisms against which the vaccine formulation is designed to act.

Vaccine formulations are then tested by any of a variety of methods as disclosed in the present disclosure, or as described below.

Antigen-Specific Recall Responses

To evaluate antigen-specific recall responses, mice are administered one or more doses of a vaccine formulation. Ten days after the last dose, lymph node cells are taken from the mice. Lymph node cells are incubated in the presence of serial dilutions of an antigen (either the antigen used in the vaccine formulation or an unrelated antigen as a negative control). Cells are subject to a proliferation assay. For example, cell cultures can be pulsed with labeled thymidine, and a "stimulation index" can be calculated from counts (of the labelling) from cultures with the antigen used in the vaccine formulation divided by counts from cultures with the unrelated antigen. Enhanced proliferation in cultures containing the antigen used in the vaccine indicates an antigen-specific recall response.

Response Profile

Lymph node cells from mice administered one or more doses of a vaccine formulation can be analyzed in terms of cell surface marker (e.g., CD4+ vs CD8+) (e.g., by flow cytometry) and/or by cytokine release (e.g., by ELISA or ELISPOT assays). Cytokine release profiles may indicate the type of immune response (e.g., type-1, type-2, or type-17). Cytokine release profiles indicating both type-1 and type-17 responses indicate a potentially effective vaccine formulation.

Tumor Growth Inhibition

Anti-tumor vaccine formulations comprise an antigen of interest that is expressed in tumor cells. These formulations can be tested for their ability to inhibit tumor growth in an appropriate animal tumor model. Controls can include one more of: adjuvant (zymosan and MONTANIDE™) only formulations (as a negative control) or formulations comprising the antigen of interest and a different adjuvant that is commonly used.

Dosing Studies

To determine a vaccine formulation's effective dose, dosing studies may be conducted using a range of amounts in each dose (e.g., ranging in amounts of the antigen of interest and/or zymosan) and/or the number of doses. Output measures can include one or more of antigen-specific recall responses, response profiles, or tumor growth inhibition (in the case of anti-cancer vaccine formulations).

Example 10: Emulsification Protocol

To obtain an emulsion comprising an antigen (e.g., a polypeptide antigen) and MONTANIDE™ ISA 51, two silicone-free syringes connected by a connector (I or T-connector) can be used to create high shear conditions in order to entrap droplets of water into a surrounding oil phase. The antigen may be dissolved in an aqueous solution, e.g., water or in a saline solution (most often PBS or NaCl 0.9% saline buffer), and one volume of this aqueous antigen solution can be mixed with one volume of MONTANIDE™ ISA 51. The mix can then be loaded into the device comprising two silicone-free syringes connected for example by an I-connector, which is used to perform a pre-emulsification step comprising multiple (e.g., about 20) low speed cycles (e.g., cycles lasting approximately 4 seconds), followed by an emulsification step comprising multiple (e.g., about 40) rapid cycles. A cycle is defined as the transfer of the whole solution (aqueous phase and adjuvant) from a first syringe to the other, followed by a transfer of the whole solution back to its syringe of origin.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize or be able to ascertain using no more than routine experimentation, many equivalents to the specific embodiments described herein. Such equivalents are intended to be encompassed by the following claims.

The invention claimed is:

1. A composition comprising:
   (a) a tumor-associated antigen;
   (b) zymosan;
   (c) mineral oil; and
   (d) mannide monooleate.

2. The composition of claim 1, wherein said composition is capable of inducing an antigen-specific T cell immune response comprising both a type-1 and a type-17 proinflammatory T cell response when said composition is administered to a subject.

3. The composition of claim 1, wherein the composition is a water-in-oil emulsion.

4. The composition of claim 1, wherein the tumor-associated antigen is a retired self-antigen.

5. The composition of claim 4, wherein the tumor-associated antigen comprises an α-lactalbumin polypeptide comprising at least 8 consecutive amino acids of SEQ ID NO: 5.

6. The composition of claim 1, wherein the ratio of antigen to zymosan in the composition is from about 10:1 (w/w) to about 1:10 (w/w).

7. The composition of claim 5, wherein the α-lactalbumin polypeptide comprises an amino acid sequence that is at least 95% identical to the amino acid sequence of SEQ ID NO: 5.

8. The composition of claim 7, wherein the α-lactalbumin polypeptide comprises an amino acid sequence of SEQ ID NO: 5.

9. The composition of claim 5, wherein the composition is a water-in-oil emulsion.

10. The composition of claim 8, wherein the composition is a water-in-oil emulsion.

* * * * *